United States Patent [19]
Craig et al.

[11] Patent Number: 5,776,941
[45] Date of Patent: Jul. 7, 1998

[54] 4-ALKYLTHIO-PYRIMIDIN-5-YLACETIC ACID DERIVATES

[75] Inventors: Gerald Wayne Craig, Basel; Martin Eberle, Bottmingen; Fritz Schaub, Aesch, all of Switzerland

[73] Assignee: Sandoz Ltd., Basel, Switzerland

[21] Appl. No.: 606,911

[22] Filed: Feb. 26, 1996

[30] Foreign Application Priority Data

Mar. 10, 1995 [GB] United Kingdom ............... 9504920

[51] Int. Cl.$^6$ ............ C07D 239/46; A01N 43/54
[52] U.S. Cl. ............ 514/269; 544/319; 544/295; 544/284; 544/238; 514/252; 514/253; 514/259
[58] Field of Search ............ 514/269, 252, 514/259, 253; 544/319, 295, 284, 238

[56] References Cited

U.S. PATENT DOCUMENTS 5,547,919  8/1996  Eberle et al. ............ 544/319

FOREIGN PATENT DOCUMENTS

| A-634405 | 1/1995 | European Pat. Off. |
| WO92/17457 | 10/1992 | WIPO |
| WO92/17458 | 10/1992 | WIPO |
| WO92/17459 | 10/1992 | WIPO |

*Primary Examiner*—John M. Ford
*Attorney, Agent, or Firm*—Lynn Marcus-Wyner; Michael P. Morris

[57] ABSTRACT

This invention relates to 2-(4-alkylthio-pyrimidin-5-yl)-acetic acid derivatives; fungicidal compositions comprising such compounds and a method of combating phytopathogenic fungi comprising applying such compounds to the fungi or their habitat.

17 Claims, No Drawings

4-ALKYLTHIO-PYRIMIDIN-5-YLACETIC ACID DERIVATES

This invention relates to novel 2-(4-alkylthio-pyrimidin-5-yl) acetic acid derivatives, the synthesis thereof and the use of said compounds for the control of phytopathogens.

It has now been found that compounds of formula I

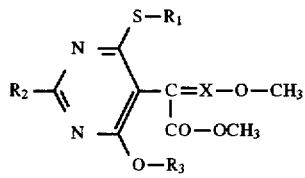

wherein $R_1$ is $C_{1-4}$alkyl, $R_2$ is hydrogen, $C_{1-4}$alkyl, or $C_{3-7}$cycloalkyl, $R_3$ is a radical

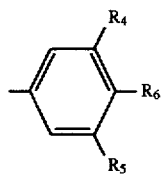

wherein $R_4$ is hydrogen, $C_{1-4}$alkyl, $C_{1-4}$haloalkyl, aryl, aryloxy, $C_{3-5}$alkenyloxy, $C_{3-5}$alkynyloxy, halogen, cyano, aryl-$C_{1-4}$alkoxy, aryloxy-$C_{1-4}$alkyl, heteroaryl, heteroaryloxy, $C_{1-4}$alkoxy, $C_{1-4}$alkoxy-$C_{1-4}$-alkoxy, cyano-$C_{1-4}$alkoxy, $C_{3-5}$alkenyl, aryloxy-$C_{1-4}$-alkoxy, $C_{3-7}$cycloalkyl, halo-$C_{3-7}$cycloalkyl, $C_{3-5}$alkynyl, $C_{1-4}$alkoxycarbonyl, —$CONR_9R_{10}$, —O—$CONR_9R_{10}$ or —$CR_8$=N—O—$R_7$, wherein each of the aromatic rings may be optionally substituted;

$R_5$ is hydrogen, halogen, $C_{1-4}$alkoxy or $C_{1-4}$alkyl, $R_6$ is hydrogen, $C_{1-4}$alkyl, $C_{1-4}$alkoxy, cyano, nitro or halogen, $R_7$ is $C_{1-4}$alkyl, $C_{3-5}$alkenyl, $C_{3-5}$alkynyl, or aryl-$C_{1-4}$alkyl, $R_8$ is hydrogen, $C_{1-4}$alkyl, $C_{1-4}$alkoxy, di-$C_{1-4}$alkylamino, $C_{1-4}$haloalkyl, halogen, cyano, $C_{1-4}$alkoxycarbonyl, or $C_{1-7}$cycloalkyl, $R_9$ and $R_{10}$ are independently hydrogen or $C_{1-14}$alkyl, or together $C_{3-6}$ alkylene or $C_{3-6}$alkylene interrupted by oxygen or sulfur, and X is CH or nitrogen;

are surprisingly effective against phytopathogens.

In the definitions of the radicals of formula I alkyl is understood to encompass straight-chain and branched alkyl groups, with branched-chain and lower alkyl being preferred. For example alkyl is methyl, ethyl, n-propyl, isopropyl, n-butyl, isobutyl, tertiary butyl or secondary butyl. Alkoxy for example encompasses methoxy, ethoxy, n-propoxy, isopropoxy, n-butyloxy, isobutyloxy, tertiary butyloxy or secondary butyloxy. Halogen designates fluorine, chlorine, bromine and iodine, with fluorine and chlorine being preferred. Haloalkyl designates straight chain or branched alkyl groups which are mono-to perhalogenated with straight-chain lower alkyl being the preferred alkyl and with fluorine perhalogenated with straight-chain lower alkyl being the preferred alkyl and with fluorine and chlorine being preferred halogens. Examples are trifluoromethyl, difluoromethyl, 2,2,2-trifluoroethyl or 2,2,3,3,3-pentafluoropropyl. Aryl stands for aromatic hydrocarbon radicals, for example phenyl, naphthyl or anthracenyl, with phenyl being preferred. The aryl radical may optionally be further substituted. Aryloxy designates an aryl radical being bounded through an oxygen atom. Examples are phenoxy, naphthyloxy or anthracenyloxy. The aryloxy radical may optionally be further substituted at the aryl part. Alkoxyalkoxy for example encompasses methoxymethoxy, ethoxymethoxy, methoxyethoxy or ethoxyethoxy. Cyanoalkoxy encompasses for example cyanomethoxy, 1-cyanoethoxy or 2-cyanoethoxy. Alkenyloxy designates for example allyloxy, 2-butenyloxy, 3-butenyloxy, 2-pentenyloxy, 2-methallyloxy, 3-pentenyloxy, 4-pentenyloxy, 2-methyl-2-butenyloxy, 3-methyl-2-butenyloxy, or 3-methyl-3-butenyloxy. Alkynyloxy is for example propargyloxy, 2-butynyloxy, 3-butynyloxy, 2-pentynyloxy, 3-pentynyloxy, 4-pentynyloxy, 2-methyl-3-butynyloxy or 2-methylpropargyloxy. Arylalkoxy is for example benzyloxy, 2-phenylethoxy or 1-phenylethoxy or 3-phenylpropoxy. The arylalkoxy may optionally be further substituted at the aryl part. Examples for aryloxyalkoxy are phenoxymethoxy, 1-phenoxyethoxy, 2-phenoxyethoxy, 3-phenoxypropoxy or 2-phenoxypropoxy. The aryloxyalkoxy may optionally be further substituted at the aryl part. Aryloxyalkyl or heteroaryloxyalkyl designate an aryl or heteroaryl radical being linked to the alkyl chain through an oxygen atom. Typical examples are phenoxymethyl, phenoxyethyl or phenoxypropyl. The aryloxyalkyl or heteroaryloxyalkyl may optionally be further substituted at the aromatic ring. Alkenyl designates for example vinyl, allyl, 2-butenyl, 3-butenyl, 2-pentenyl, 2-methallyl, 3-pentenyl, 4-pentenyl, 2-methyl-2-butenyl, 3-methyl-2-butenyl, or 3-methyl-3-butenyl. Alkynyl is for example ethynyl, propargyl, 2-butynyl, 3-butynyl, 2-pentynyl, 3-pentynyl, 4-pentynyl, 2-methyl-3-butynyl or 1-methylpropargyl. Heteroaryl stands for aromatic 5- or 6-membered cyclic radicals comprising one, two or three ring atoms selected from nitrogen, oxygen and sulfur, which may also be in condensed form with another heteroaryl radical or aryl radical. The heteroaryl may optionally be further substituted. Examples are pyridyl, pyrimnidinyl, thienyl, oxazolyl, oxadiazolyl, triazolyl, thiadiazolyl, furyl, isoxazolyl, thiazolyl, imidazolyl, pyridazinyl, quinolinyl, quinazolinyl, benzimidazolyl, pyrazolyl, benzothiazolyl, benzoxazolyl, and the like. Heteroaryloxy designates a heteroaryl radical being linked through an oxygen bridge. The alkylene bridges optionally formed by $R_9$ and $R_{10}$, respectively, together with the nitrogen atom to which they are attached form e.g. a pyrrolidinyl or piperidinyl radical bound through the nitrogen atom. Where the alkylene chain is interrupted by oxygen or sulfur the group $NR_9R_{10}$ may e.g. stand for N-morpholinyl or N-thiomorpholinyl. Examples for alkoxycarbonyl are e.g. methoxycarbonyl, ethoxycarbonyl or propoxycarbonyl. Cycloalkyl stand for cyclopropyl, cyclobutyl, cyclopentyl, cyclohexyl or cycloheptyl, with cyclohexyl and cyclopentyl being preferred. A preferred example for halocycloalkyl is 2,2-difluorocyclopropyl.

In radicals being combined from various other definitions, each of the definitions has the meanings given for the partial definition separately.

The above aryl and heteroaryl radicals may be further substituted. Where aryl or heteroaryl is substituted, it is preferably substituted by one or two radicals selected from the group comprising halogen, $C_{1-4}$alkyl, $C_{1-4}$alkoxy, $C_{1-4}$haloalkyl, $C_{1-4}$haloalkoxy, cyano, nitro, —$CR_8$=N—O—$R_7$, phenyl or phenoxy, which phenyl or phenoxy radicals may in turn be substituted with one or two radicals selected from halogen. $C_{1-4}$alkyl, $C_{1-4}$alkoxy, $C_{1-4}$haloalkyl, cyano or nitro.

Among the compounds of formula I those are of particular interest wherein $R_2$ and $R_8$ are independly each hydrogen or methyl.

Further preferred subgroups of compounds of formula I are those wherein either a) $R_1$ is methyl, or b) $R_2$ is methyl, or c) $R_5$ is hydrogen or methyl, or d) $R_6$ is hydrogen, or e) X is CH, or f) $R_4$ is $C_{1-4}$alkyl, $C_{1-4}$haloalkyl, phenyl, phenoxy, cyanophenoxy, chlorophenoxy, methylphenoxy, dimethylphenoxy, trifluoromethylphenoxy, halogen, cyano, benzyloxy, isoxazolyl, benzothiazolyloxy, $C_{1-4}$alkoxy, or the group —C(CH$_3$)—N—O—R$_7$, wherein R$_7$ is $C_{1-4}$alkyl, allyl, propargyl or benzyl, or g) $R_4$ is pyrazolyl.

A further preferred subgroup of compounds of formula I is wherein R, and $R_2$ are methyl, $R_5$ and $R_6$ are hydrogen and $R_4$ is $C_{1-4}$alkyl, $C_{1-4}$haloalkyl, phenyl, phenoxy, cyanophenoxy, chlorophenoxy, methylphenoxy, dimethylphenoxy, trifluoromethylphenoxy, halogen, cyano, benzyloxy, isoxazolyl, benzothiazolyloxy, $C_{1-4}$alkoxy, or the group —C(CH$_3$)=N—O—R$_7$, wherein R$_7$ is C$_1$alkyl, allyl, propargyl or benzyl.

Another preferred subgroup of compounds of formula I is wherein $R_1$ and $R_2$ are methyl, $R_5$ and $R_6$ are hydrogen and $R_4$ is pyrazolyl.

Among these subgroups those compounds are preferred wherein X is CH.

Another preferred subgroup of compounds corresponds to the subformula Ia

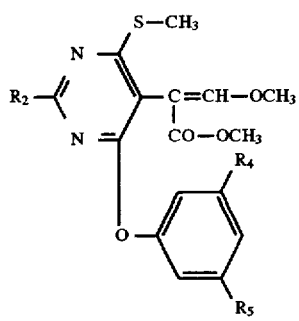

wherein $R_2$ is hydrogen or methyl, $R_4$ is hydrogen, isoxazolyl, phenyl, $C_{1-4}$alkyl, —CH$_2$—O—phenyl, —CH$_2$—O—CH$_2$-phenyl, —C(CH$_3$)=N—O—C$_{1-4}$alkyl, —C(CH$_{3-4}$) =N—O—C$_3$-alkenyl, —C(CH$_3$)=N—OCH$_2$-phenyl, wherein phenyl may be optionally substituted by one or two radicals independently selected from halogen, $C_{1-4}$alkyl, $C_{1-4}$alkoxy or cyano; or is phenoxy optionally substituted by one to three radicals selected from $C_{1-4}$alkyl, cyano, nitro, halogen, $C_{1-4}$haloalkyl, $C_{1-4}$alkoxy, or $C_{1-4}$haloalkoxy;

$R_5$ is hydrogen or methyl.

Alternatively in the subgroup of formula Ia $R_2$ and $R_5$ are as defined and $R_4$ is pyrazolyl.

Preferred individual compounds of formula I are: methyl α-[2-methyl4-methylthio-6-(3-trifluoromethyl-phenoxy)-pyrimidin-5-yl]-β-methoxyacrylate;

methyl α-[2-methyl4-methylthio-6-(3-(2-cyanophenoxy)-phenoxy)-pyrimidin-5-yl]-β-methoxyacrylate;

methyl α-[2-methyl4-methylthio-6-(3-methoxyphenoxy)-pyrimidin-5-yl]-β-methoxyacrylate;

methyl α-[2-methyl4-methylthio-6-(3-(3-chlorobenzyloxy)-phenoxy)-pyrimidin-5-yl]-β-methoxyacrylate;

methyl α-[2-methyl4-methylthio-6-(3-isopropyl-5-methyl-phenoxy)-pyrimidin-5-yl]-β-methoxyacrylate;

methyl α-[2-methyl4-methylthio-6-(3-(1-methyl-2-ethoxyimino)-phenoxy)-pyrimidin-5-yl]-β-methoxyacrylate;

methyl α-[4-methylthio-6-(3-(1-methyl-2-ethoxyimino)-phenoxy)-pyrimidin-5-yl]-β-methoxyacrylate;

methyl α-[2-methyl4-methylthio-6-(3-(4-chlorophenyl)-phenoxy)-pyrimidin-5-yl-]-β-methoxyacryate;

methyl α-[2-methyl-4-methylthio-6-(3-(3-cyanophenyl)-phenoxy)-pyrimidin-5-yl]-p-methoxyacrylate;

methyl α-[2-methyl4-methylthio-6-(3-(2-methylphenyl)-phenoxy)-pyrimidin-5-yl]-β-methoxyacrylate;

methyl 2-methoximino-2-[2-methyl4-methylthio-6-(3-tert.-butyl-phenoxy)-pyrimidin-5-yl]-acetate; and methyl 2-methoxyimino-2-[2-methyl4-methylthio-6-(3-(2-cyanophenoxy)-phenoxy) -pyrimidin-5-yl]-acetate.

The double bond of the acrylic acid structure in the compounds of formula I may be in E- or Z-form. In this document the E- and Z-forms are identified where meant specifically. In all other cases mixtures of the two isomers are intended. Where E- and Z-isomers are obtained during synthesis they may be separated by known techniques, such as crystallisation, chromatography or distillation. In the described methods of preparation preferably the E-forms are obtained.

Compounds of formula I may be obtained by 0-methylation of a compound of formula II

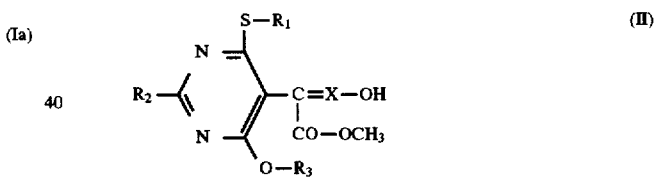

wherein $R_1$, $R_2$, $R_3$ and X are as defined above.

The O-methylation (II→I) can be carried out in a manner known per se for the preparation of 3-methoxyacrylates employing conventional methylation agents. Examples of suitable methylation agents include methyl iodide and dimethyl sulphate. The O-methylation is conveniently carried out in the presence of a base. The reaction temperature will conveniently lie in the range of from 0° C. to the boiling point of the reaction mixture, e.g. at about ambient temperature. Inert solvents may be used where desired. Examples of suitable bases include alkaline metal hydrides such as sodium hydride, alkaline metal alcoholates such as sodium methylate or alkaline metal carbonates. Examples of suitable inert solvents include aromatic hydrocarbons such as benzene and toluene; ethers such as diethyl ether, tetrahydrofuran and 1,2-dimethoxyethane; polar solvents such as dimethylformamide, dimethyl sulfoxide, alcohols such as methanol; acetone or a mixture comprising two or more of them. The desired end-product is isolated and purified according to known techniques, for example by evaporation of solvent, chromatography and crystallisation.

The compounds of formula I are basic in nature. They may form salts with sufficiently strong acids such as HCl and HBr.

The compounds of formula II wherein X is CH may be obtained by reaction of compounds of formula III

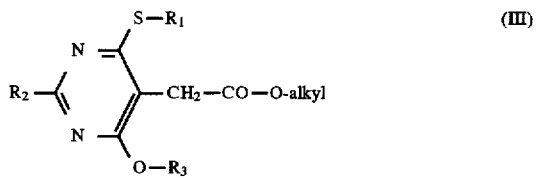

wherein $R_1$, $R_2$ and $R_3$ are as defined above and alkyl is $C_{1-10}$-alkyl, with a formylating agent, e.g. N,N-diformylmethylamine, or methyl formate in the presence of a base.

This reaction is essentially a Claisen reaction and may be carried out under the conditions known for such reaction. The reaction (III→II) may be carried out in an inert solvent. Examples of suitable solvents are as described for the O-methylation of the compounds of formula II. Examples of suitable bases are such typically used for a Claisen reaction such as alkaline metal alcoholates, e.g. sodium methylate; alkaline metal hydrides, e.g. sodium hydride; and lithium amides or sodium amides, e.g. lithium diethylamide. The reaction temperature may vary within wide ranges, e.g. from 0° C. to the boiling point of the reaction mixture and is preferably at or near ambient temperature.

In an alternative process the compounds of formula II may also be obtained by reacting the compounds of formula III with a pre-prepared 1:1-adduct of dimethylformamide and dimethylsulfate in the presence of a strong base, such as t-BuOK and hydrolysing the obtained intermediate of formula IIIa

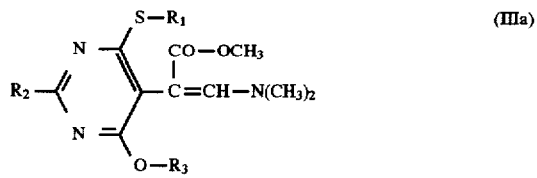

wherein $R_1$, $R_2$ and $R_3$ are as defined above.

This reaction variant is preferably carried out in an inert solvent at temperature between –70° C. to –30° C., preferably –60° C. to –40° C. Suitable solvents are ethers like tetrahydrofuran, dioxane, diethylether or glyme. Suitable bases are e.g. alkaline alcolates like t-BuOK; or alkaline hydrides like NaH, KH. The hydrolysing step is typically done in a two-phase system, by adding water, and at a temperature of 0° C. to +40° C., preferably at room temperature.

The compounds of formula II wherein X is N may be obtained by reacting a compound of formula III with an alkyl nitrite in the presence of a base, optionally in the presence of an inert solvent. In a variant of this process the compounds of formula II wherein X is N may also be obtained by reacting a compound of formula III with an alkyl nitrite in the presence of hydrochloric acid, optionally in an inert solvent. The reaction temperature will conveniently lie in the range of from –40° C. to +20° C. e.g. at about –20° C. to 0° C. Inert solvents may be used where desired. Examples of suitable bases include alkaline metal hydrides such as sodium hydride and alkaline metal alcoholates such as potassium tert.-butylate. Examples of suitable inert solvent include aromatic hydrocarbons such as benzene and toluene; ethers such as diethyl ether, tetrahydrofuran and 1,2-dimethoxyethane; polar solvent such as dimethylformamide, dimethyl sulfoxide, alcohols such as tert.-butanol; or a mixture comprising two or more of them.

In a variant of the two-step process (III→II→I), the compounds of formula I may be obtained by a single-vessel reaction from compounds of formula m, without isolation and purification of the intermediate compounds of formula II.

The acetic acid esters of formula ImI may be obtained from compounds of formula IV

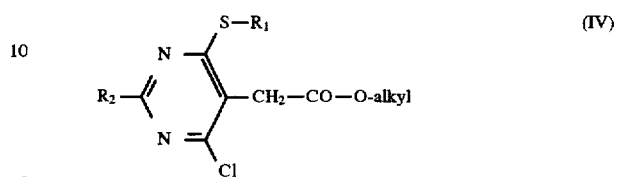

wherein $R_1$ and $R_2$ are as defined above and alkyl is $C_{1-10}$alkyl, by reacting it with an alcohol of formula V

wherein $R_3$ is as defined above in the presence of a base and an inert solvent. Suitable bases and solvents are as for (II→I).

The compounds of formula IV may be obtained by reacting a compound of formula VI

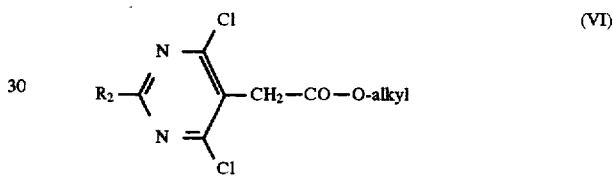

wherein $R_2$ is as defined above and alkyl is $C_{1-10}$alkyl, with a mercaptane of formula VII

wherein $R_1$ is as defined above, in the presence of a base.

This reaction is preferably carried out in an inert solvent such as an ether, e.g. glyme (dimethoxyethane). Suitable bases are sodium hydride, sodium methylate or the like. In a preferred variant the base is reacted with the mercaptane first to give the sodium salt, which may then be reacted with the compound of formula VI without the presence of a base.

Another variant comprises reducing an alkyl dissulfide $R_1$—SS—$R_1$ wherein $R_1$ is as defined above with a suitable reducing agent such as alkaline borohydride ($NaBH_4$) or alkaline metal hydride (NaH, $CaH_2$, $LiAlH_4$) followed by reaction with compound of formula VI. This reaction is preferably carried out in an inert solvent such as an ether, e.g. glyme, tetrahydrofuran, or dimethylformamnide (DMF) or an organic hydrocarb on like benzene or toluene.

The intermediates of formulae II, II, IIIa and IV have e specially been developed for the synthesis of compounds of formula I. The y therefore constitute a part of present invention.

The starting materials of formulae V, VI, and VII are known, or may be prepared in analogy to known processes.

The compounds of formula I are effective against phytopathogens.

Their advantageous fungicidal activity is established by in vivo tests with test concentrations from 0.1 to 500 mg a.i./l against Uromyces appendiculatus on pole beans, against Puccinia triticina on wheat, against Sphaerotheca fuliginea on cucumber, against Erysiphe graminis on wheat and barley, against *Podosphaera leucotricha* on apple, against *Uncinula necator* on grape vine, against *Leptosphaeria nodorum* on wheat, against *Cochliobolus sativus* and *Pyrenophora graminea* on barley, against Venturia inequalis on apple, against *Phytophthora infestans* on tomato and against *Plasmopara viticola* on grape vine.

Many of the compounds of formula I have an excellent plant tolerance and a systemic action. The compounds of the invention are therefore indicated for treatment of plant, seeds and soil to combat phytopathogenic fungi, e.g. Basidiomycetes of the order Uredinales (rusts) such as Puccinia spp, Hemileia spp, Uromyces spp; and Ascomycetes of the order Erysiphales (powdery mildew) such as Erysiphe ssp, Podosphaera spp, Uncinula spp, Sphaerotheca spp; as well as Cochliobolus; Pyrenophora spp; Venturia spp; Mycosphaerella spp; Leptosphaeria; Deuteromycetes such as Pyricularia, Pellicularia (Corticium), Botrytis; and Oomycetes such as Phytophthora spp, Plasmopara spp.

The compounds of formula I are particularly effective against powdery mildew and rust, pyrenophora and leptosphaeria fungi, in particular against pathogens of monocotyledoneous plants such as cereals, including wheat and barley.

The amount of compound of the invention to be applied, will depend on various factors such as the compound employed, the subject of the treatment (plant, soil, seed), the type of treatment (e.g. spraying, dusting, seed dressing), the purpose of the treatment (prophylactic or therapeutic), the type of fungi to be treated and the application time.

In general, satisfactory results are obtained, if the compounds of the invention are applied in an amount of from about 0.01 to 2.0, preferably about 0.02 to 1 kg/ha, in the case of a plant or soil treatment; e.g. 0.04 to 0.500 kg of active ingredient (a.i.) per ha in field crops such as cereals, or concentrations of 4 to 50g of a.i. per hl in crops such as fruits, vineyards and vegetables (at an application volume of from 300 to 1000 l/ha—depending on the size or leaf volume of the crop—which is equivalent to an application rate of approximately 30–500 g/ha). The treatment can, if desired, be repeated, e.g. at intervals of 8 to 30 days.

Where the compounds of the invention are used for seed treatment, satisfactory results are in general obtained, if the compounds are used in an amount of from about 0.05 to 0.5, preferably about 0.1 to 0.3 g/kg seeds.

The term soil as used herein is intended to embrace any conventional growing medium, whether natural or artificial.

The compounds of the invention may be used in a great number of crops, such as soybean, coffee, ornamentals (i.a. pelargonium, roses), vegetables (e.g. peas, cucumber, celery, tomato and bean plants), sugarbeet, sugarcane, cotton, flax, maize (corn), vineyards, pomes and stone fruits (e.g. apple, pears, prunes) and in cereals (e.g. wheat, oats, barley, rice).

The invention also provides fungicidal compositions, comprising as a fungicide a compound of formula I in association with a agriculturally acceptable diluent (hereinafter diluent). They are obtained in conventional manner, e.g. by mixing a compound of the invention with a diluent and optionally additional ingredients, such as surfactants.

The term diluents as used herein means liquid or solid agriculturally acceptable material, which may be added to the active agent to bring it in an easier or better applicable form, resp. to dilute the active agent to a usable or desirable strength of activity. Examples of such diluents are talc, kaolin, diatomaceous earth, xylene or water.

Especially formulations used in spray form,such as water dispersible concentrates or wettable powders, may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent, from 0 to 20% agriculturally acceptable surfactant and from 10 to 99.99% diluent(s). Concentrated forms of composition, e.g. emulsion concentrates, contain in general from about 2 to 90%, preferably from between 5 and 70% by weight of active agent. Application forms of formulation contain in general from 0.0005 to 10% by weight of a compound of the invention as active agent; typical spray-suspensions may, for example, contain from 0.0005 to 0.05, e.g. 0.0001, 0.002 or 0.005% by weight of active agent.

In addition to the usual diluents and surfactants, the compositions of the invention may comprise further additives with special purposes, e.g. stabilisers, desactivators (for solid formulations or carriers with an active surface), agents for improving the adhesion to plants, corrosion inhibitors, anti-foaming agents and colorants. Moreover, further fungicides with similar or complementary fungicidal activity, e.g. sulphur, chlorothalonil, euparen; a guanidine fungicide such as guazatine; dithiocarbamates such as mancozeb, maneb, zineb, propineb; trichloromethane sulphenylphthalimides and analogues such as captan, captafol and folpet; benzimidazoles such as carbendazim, benomyl; azoles such as cyproconazole, flusilazole, flutriafol, hexaconazole, propiconazole, tebuconazole, epoxiconazole, triticonazole, prochloraz; morpholines such as fenpropimorph, fenpropidine, or other beneficially-acting materials, such as cymoxanil, oxadixyl, metalaxyl, or insecticides may be present in the formulations.

Examples of plant fungicide formulations are as follows:

a. Wettable Powder Formulation

10 Parts of a compound of formula I are mixed and milled with 4 parts of synthetic fine silica, 3 parts of sodium lauryl sulphate, 7 parts of sodium lignin sulphonate and 66 parts of finely divided kaolin and 10 parts of diatomaceous earth until the mean particle size is about 5 micron. The resulting wettable powder is diluted with water before use to a spray liquor which may be applied by foliar spray as well as by root drench application.

b. Granules

Onto 94.5 parts by weight of quartz sand in a tumbler mixer are sprayed 0.5 parts by weight of a binder (non-ionic tenside) and the whole thoroughly mixed. 5 parts by weight of a compound of formula I invention are then added and thorough mixing continued to obtain a granulate formulation with a particle size in the range of from 0.3 to 0.7 mm (where required, the granules may be dried by the addition of 1 to 5% by weight of talcum). The granules may be applied by incorporation into the soil adjacent to the plants to be treated.

c. Emulsion Concentrate

10 Parts by weight of a compound of formula I are mixed with 10 parts of weight of an emulsifier and 80 parts by weight of xylene. The thus obt ained conce ntrat e is diluted with water to form an emulsion of the desired concentration, prior to application.

d. Seed Dressing

45 Parts of a compound of formula I are mixed with 1.5 parts of diamyl phenoldecaglycolether ethylene oxide adduct, 2 parts of spindle oil, 51 parts of fine talcum and 0.5 parts of colorant rhodanin B. The mixture is ground in a contraplex mill at 10,000 rpm until an average particle size of less than 20 microns is obtained. The resulting dry powder has good adherence and may be applied to seeds, e.g. by mixing for 2 to 5 minutes in a slowly turning vessel.

The following examples further illustrate the present invention. All temperatures are in centigrade.

EXAMPLE 1

Methyl α-|2-methyl-4-methylthio-6-(3-(2-cyanophenoxy)-phenoxy)-pyrimidin-5-yl]-β-methoxyacrylate

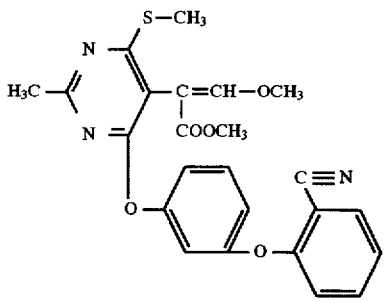

a) Methyl 2-(4-chloro-2-methyl-6-methylthio-pyrimidin-5-yl)-acetate

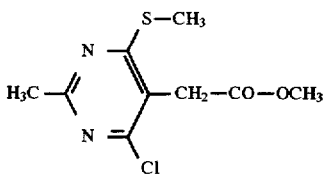

Methyl 2-(4,6-dichloro-2-methyl-pyrimidin-5-yl)-acetate (40 g) and sodium thiomethoxide (13 g) are suspended in glyme (200 ml) and stirred at room temperature for 2.5 hours. The mixture is poured into water and extracted with ethyl acetate and the organic phase dried over anhydrous sodium sulfate yielding the methyl 2-(4-chloro-2-methyl-6-methylthio-pyrimidin-5-yl)-acetate after evaporation, m.p. 74° C. NMR (CDCl$_3$): 3.89 (s, 2H); 3.70 (s, 3H); 2.63 (s, 3H); 2.55 (s, 3H).

b) Methyl 2-[2-methyl-4-methylthio-6-(3.(2-cyanophenoxy)-phenoxy)pyrimidin-5-yl]-acetate

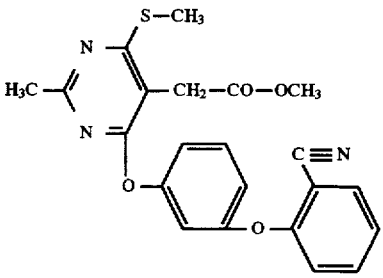

A solution of methyl 2-(4-chloro-2-methyl-6-methylthio-pyrimidin-5-yl)-acetate (5.5 g) in DMF (80 ml) is added to a suspension of anhydrous potassium carbonate (5.6 g) and 3-(2-cyanophenoxy)phenol (5.1 g) and copper iodide (1 g) in DMF at room temperature. The mixture was heated to +120° C. for 2 hours and then cooled. The mixture is poured into water and extracted successively with ethyl acetate (2×50 ml) and the organic phase dried over anhydrous sodium sulfate. Evaporation and drying under high vacuum gives the methyl 2-[2-methyl-4-methylthio-6-(3-(2-cyanophenoxy)-phenoxy)-pyrimidin-5-yl]-acetate, as a crude product in form of a yellow oil. NMR (CDCl$_3$): 6.18–6.84 (m, 3H); 3.74 (s, 2H); 3.69 (s, 3H); 2.85 (m, 1H); 2.51 (s, 3H); 2.45 (s, 3H); 2.34 (s, 3H); 1.22 (d, 6H).

c) A mixture of 18-crown-6 (200 mg) and potassium t-butylate (3.5 g) is stirred in glyme at room temperature for 20 minutes under nitrogen atmosphere. The solution is then cooled to –50° C. and a solution of methyl 2-[2-methyl-4-methylthio-6-(3-(2-cyanophenoxy)-phenoxy)-pyrimidin-5-yl]-acetate, dissolved in glyme is added dropwise over 30 minutes. The solution is stirred for 15 minutes followed by the dropwise addition of a solution of pre-prepared 1:1 adduct of dimethylsulfate-dimethylformamide 11.5 ml). The adduct is prepared by taking equal equivalents of dimethylsulfate and dimethylformamide and warming to +60° C. for 2 hours. The cooled solution containing 1:1 adduct is used as such where described in the following procedures. The cooling bath is removed and the temperature allowed to warm to room temperature. The mixture is further stirred 2 hours until reaction is complete and then poured into aqueous sodium bicarbonate and extracted with ethyl acetate (2×60 ml) and the organic phase is dried over anhydrous sodium sulfate. Evaporation of solvent and drying under high vacuum gives a viscous oil whose NMR was consistent with the intermediate methyl α-|2-methyl-4-methylthio-6-(3-(2-cyanophenoxy)-phenoxy)-pyrimidin-5-yl]-β-dimethylamino-acrylate.

NMR (CDCl$_3$): 6.80–7.68 (m, 8H); 3.60 (s, 3H); 2.85 (s, 6H); 2.5 (s, 3H); 2.50 3H).

The intermediate oil (4.8 g) is dissolved in ether (80 ml) and at +10° C. combined with p-toluenesulfonic acid (2.9 g) dissolved in water (80 ml). Stirring overnight at room temperature gives complete hydrolysis. The two phases are separated after neutralization with aqueous sodium bicarbonate and the aqueous phase extracted with ethyl acetate (2×60 ml). The combined organic phases are dried over sodium sulfate and the solvent is removed by evaporation. The resulting viscous oil is then dissolved in dimethylformamide (60 ml) containing dimethyl sulfate (1.9 ml). Anhydrous potassium carbonate (4.0 g) is added at +10° C. and stirred at room temperature for 3 hours to give complete methylation to methyl α-[2-methyl4-methylio -6-(3-isopropyl-5-methyl-phenoxy)-pyrimidin-5-yl]-β-methoxyacrylate. The reaction mixture is poured into water and extracted with ethyl acetate (3×60 ml) and the organic phase is dried over anhydrous sodium sulfate. Evaporation of solvent followed by silica column chromatography gives isolation of the product as a crystalline solid; m.p. 144° C. NMR (CDCl$_3$): 6.78–7.69 (m, 8H); 3.85 (s, 3H); 3.68 (s, 3H); 2.52 (s, 3H); 2.48 (s, 3H).

EXAMPLE 2

Methyl α-[2-methyl-4-methylthio-6-(3-trifuoromethyl-phenoxy)-pyrimidin-5-yl]-β-methoxyacrylate

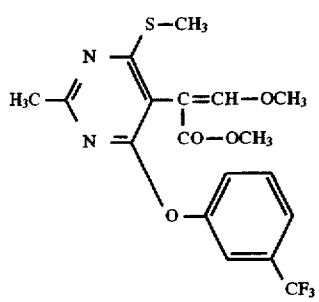

a) Methyl 2-[2-methyl-4-methylthio-6-(3-trifluoromethyl-phenoxy)-pyrimidin5-yl]-acetate

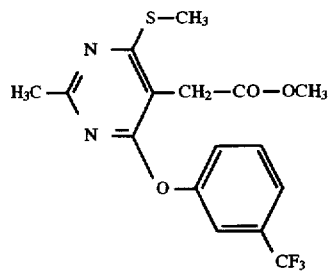

A solution of methyl 2-(4-chloro-2-methyl-6-methylthio-pyrimidin-5-yl)-acetate (4.9 g) in DMF is added to a suspension of anhydrous potassium carbonate 5.6 g), copper iodide (1.0 g) and 3-trifluoromethylphenol (3.3 g) in DMF (50 ml) at room temperature. The mixture is heated to +120° C. for 90 minutes and then cooled. The cooled mixture is poured into water and extracted successively with ethyl acetate (2×50 ml) and then the organic phase is dried over anhydrous sodium sulfate. Evaporation and drying under high vacuum gives the methyl 2-[2-methyl-4-methylthio-6-(3-trifluoromethyl-phenoxy)-pyrimidin-5-yl]-acetate in form of a dark oil. NMR (CDCl$_3$): 7.25–7.55 (m, 4H); 3.78 (s, 3H); 3.70 (s, 3H); 2.62 (s, 3H); 2.46 (s, 3H).

b) A mixture of 18-crown-6 (100 mg) and potassium t-butylate (5.0 g) is stirred in glyme at room temperature for 20 minutes under nitrogen atmosphere. The solution is then cooled to −50° C. and a solution of the methyl 2-[2-methyl-4-methylthio-6-(3-trifluoromethyl-phenoxy) -pyrimidin-5-yl]-acetate (5.6 g) dissolved in glyme is added dropwise over 30 minutes. The solution is stirred 15 minutes followed by the dropwise addition of a solution of pre-prepared 1:1 adduct of dimethylsulfate -dimethylformamide (10.5 ml). The cooling bath is removed and the temperature is allowed to warm to room temperature. The mixture is further stirred 2 hours until reaction is complete and then poured into aqueous sodium bicarbonate and extracted with ethyl acetate (2×60 ml) and the organic phase is dried over anhydrous sodium sulfate. Evaporation of solvent and drying under high vacuum gives a viscous oil whose NMR is consistent with the intermediate methyl α-[2-methyl-4-methylthio-6-(3-trifluoromethyl-phenoxy)-pyrimidin-5-yl]-β-dimethylamino acrylate; NMR (CDCl$_3$): 7.20–7.69 (m, 4H); 3.60 (s, 3H); 2.85 (s, 3H); 2.52 (s, 3H); 2.48 (s, 3H).

The intermediate oil (6.8 g) is dissolved in ether (40 ml) and at +10° C. combined with p-toluenesulfonic acid (4.7 g) dissolved in water (40 ml). Stirring overnight at room temperature gives complete hydrolysis. The two phases are separated after neutralization with aqueous sodium bicarbonate and the aqueous phase is extracted with ethyl acetate (2×60 ml). The combined organic phases are dried over sodium sulfate and the solvent is removed by evaporation. The resulting viscous oil is then dissolved in dimethylformamide (60 ml) containing dimethyl sulfate (4.0 ml). Anhydrous potassium carbonate (7.0 g) is added at +10° C. and stirred at room temperature for 3 hours to give complete methylation to methyl α-[2-methyl-4-methylthio -6-(3-trifluoromethyl-phenoxy)-pyrimidin-5-yl]-p-methoxyacrylate. The reaction mixture is poured into water and extracted with ethyl acetate (3×60 ml) and the organic phase is dried over anhydrous sodium sulfate. Evaporation of solvent followed by silica column chromatography gives isolation of the product as a solid. 3.99; m.p. 92° C. NMR(CDCl$_3$):7.20–7.61 (m, 5H); 3.50 (s, 3H), 3.70 (s, 3H); 2.55 (s, 3H); 2.50 (s, 3H).

EXAMPLE 3

Methyl 2-methoximino-2-[2-methyl-4-methylthio-6-(3-(2-cyanophenoxy)-phenoxy -pyrimidin-5-yl]-acetate

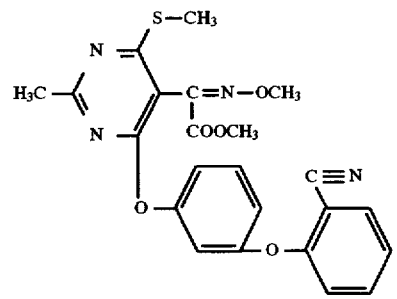

A mixture of 18-crown-6 (50 mg) and potassium tert.-butylate (1.8 g) is stirred in glyme at room temperature for 15 minutes under nitrogen atmosphere. The solution is then cooled to −30° C. and a solution of methyl 2-[2-methyl4-methylthio-6-(3-(2-cyanophenoxy)-phenoxy)-pyrimidin-5-yl]-acetate (4.6 g) dissolved in glyme and tert-butyl nitrite (3.5 ml) is added dropwise over 30 minutes and the stirring is continued for 1.5 hours with warming to room temperature. The mixture is cooled to −20° C. followed by addition of a saturated aqueous solution of ammonium chloride (26 ml) and further stirring for 4 hours with warming to room temperature. The mixture is then partioned between water and ethyl acetate (3×60 ml) and dried over anhydrous sodium sulfate. Evaporation of solvent gives an oil which was dissolved in dimethylformamide (60 ml) containing methyl iodide (3.4 ml). Sodium hydride (0.4 g) was added at −20° C. and the mixture is stirred at room temperature for 3 hours to give complete methylation to methyl 2-methoximino-2-[2-methyl4-methylthio-6-(3-(2-cyanophenoxy)-phenoxy)-pyrimidin -5-yl]-acetate. The reaction mixture is poured into water and extracted with ethyl acetate (3×60 ml) and the organic phase is dried over anhydrous sodium sulfate. Evaporation of solvent followed by silica column chromatography gives isolation of the product as a crystalline solid. m.p. 126° C. NMR (CDCl$_3$): 6.78–7.69 (m, 8H); 4.12 (s, 3H); 3.86 (s, 3H); 2.57 (s, 3H); 2.5 (s, 3H).

EXAMPLE 4

Methyl 2-methoximino-2[2-methyl-4-methylthio-6-(3-trifluoromethyl phenoxy)-pyrimidin-5-yl]-acetate

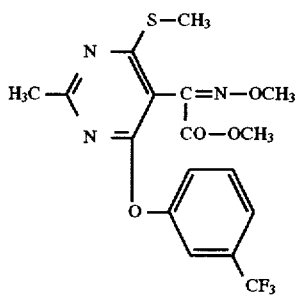

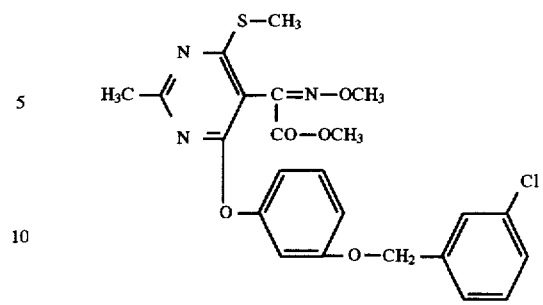

A mixture of 18-crown-6 (50 mg) and potassium t-butylate (1.8 g) in glyme (50 ml) is stirred at room temperature for 15 minutes under nitrogen atmosphere. The solution is then cooled to −30° C. and a solution of methyl 2-[2-methyl-4-methylthio-6-(3-trifluoro -phenoxy)-pyrimidin-5-yl]-acetate (4.0 g) dissolved in glyme and tert-butyl nitrite (3.5 ml) is added dropwise over 30 minutes and stirring is continued for 1.5 hours. The temperature is allowed to warm to −20° C. followed by addition of a solution of ammonium chloride and further stirring for 3 hours. The mixture is then partitioned between water and ethyl acetate (3×60 ml) and dried over anhydrous sodium sulfate. Evaporation of solvent gives an oil which was dissolved in dimethylformamide (60 ml) containing dimethyl sulfate (1.6 g). Anhydrous potassium carbonate (1.8 g) is added at +10° C. and the mixture is stirred at room temperature for 3 hours to give complete methylation to methyl 2-methoximino-2-[2-methyl4-methylthio-6-(3-trifluoromethyl -phenoxy)-pyrimidin-5-yl]-acetate. The reaction mixture is poured into water and extracted with ethyl acetate (3×60 ml) and the organic phase is dried over anhydrous sodium sulfate. Evaporation of solvent followed by silica column chromatography gives isolation of the major product (1.2 g) as a yellowish oil.

EXAMPLE 5

Methyl 2-methoximino-2-[2-methyl-4-methylthio-6-(3-(3-chlorobenzyloxy)-phenoxy) -1)-pyrimidin-5-yl]-acetate A mixture of 18-crown-6 (50 mg) and potassium tert-butylate (1.68 g) in glyme (50 ml) is stirred at room temperature for 15 minutes under nitrogen atmosphere. The solution is then cooled to −30° C. and a solution of methyl 2-[2-methyl4-methylthio-6-(3-(3-chlorobenzyloxy)-phenoxy)-pyrimidin-5-yl]-acetate (4.45 g) dissolved in glyme and tert-butyl nitrite (3.25 ml) is added dropwise over 30 minutes and stirring is continued for 1.5 hours. The temperature is allowed to warm to −20° C. followed by addition of a solution of ammonium chloride and further stirring for 3 hours. The mixture is then partitioned between water and ethyl acetate (3×60 ml) and dried over anhydrous sodium sulfate. Evaporation of solvent gives an oil which was dissolved in dimethylformamide (60 ml) containing dimethyl sulfate (1.6 g). Anhydrous potassium carbonate (1.8 g) is added at +10° C. and the mixture is stirred at room temperature for 3 hours to give complete methylation to methyl 2-methoximino-2-[2-methyl-4-methylthio-6-(3-(3-chlorobenzyloxy)-phenoxy)-pyrimidin-5-yl]-acetate. The reaction mixture is poured into water and extracted with ethyl acetate (3×60 ml) and the organic phase is dried over anhydrous sodium sulfate. Evaporation of solvent followed by silica column chromatography gives isolation of the major product (2.13 g) as a yellow oil. NMR (CDCl₃) : 6.40–7.42 (m, 8H); 5.02 (s, 2H); 4.12 (s, 3H); 3.85 (s, 3H); 2.58 (s, 3H); 2.45 (s, 3H).

The compounds of the following tables are obtained in analogous manner. phenyl

TABLE 1

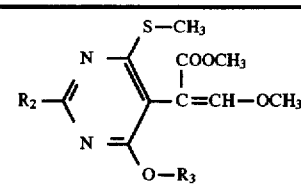

| Comp. No. | R₂ | R₃ | physical data ¹H-NMR (CDCl₃) or/and m.p. |
|---|---|---|---|
| 1.01 | CH₃ | 3-biphenylyl | 7.00–7.62(m, 10H);3.89 (s, 3H); 3.72(s, 3H); 2.52 (s, 3H); 2.49(s, 3H). |
| 1.02 | H | 3-biphenylyl | 8.55(s, 1H), 7.10–7.61(m, 10H); 3.95(s, 3H); 3.75(s, 3H); 2.55 (s, 3H). |
| 1.03 | H | 3-trifluoromethylphenyl | 8.50(s, 1H); 8.65(s, 1H); 7.20–7.60 (m, 4H); 3.90(s, 3H); 3.70 (s, 3H); 2.60(s, 3H). |
| 1.04 | CH₃ | 3-trifluoromethylphenyl | yellow oil; 7.60(s, 1H); 6.19–7.48(m, 4H); 3.88(s, 3H); 3.78(s, 3H); 2.52(s, 3H); 2.45 (s, 3H). |
| 1.05 | CH₃ | 3-phenoxyphenyl | |

TABLE 1-continued

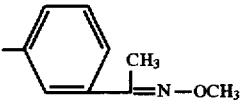

| Comp. No. | R₂ | R₃ | physical data ¹H-NMR (CDCl₃) or/and m.p. |
|---|---|---|---|
| 1.06 | CH₃ | 3-chlorophenyl | |
| 1.07 | H | 3-phenoxyphenyl | |
| 1.08 | CH₃ | 3-tert.butylphenyl | 7.60(s, 1H), 4.82–7.30(m, 4H); 3.89(s, 3H); 3.70(s, 3H); 2.52 (s, 3H); 2.46(s, 3H), 1.39 (s, 9H). |
| 1.09 | CH₃ | 3-methylphenyl | |
| 1.10 | CH₃ | 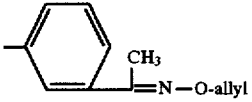 | 7.60(s, 1H), 7.00–7.46(m, 4H), 3.95(s, 3H); 3.70(s, 3H); 3.42 (5, 3H); 2.52(s, 3H); 2.48 (s, 3H); 2.20(s, 3H). |
| 1.11 | CH₃ | 3-methyl-5-isopropylphenyl | yellow oil; 7.58(s, 1H); 6.55–6.82(m, 3H); 3.86 (s, 3H), 3.70(s, 3H); 2,52 (s, 3H), 2.46 (s, 3H); 2.30 (s, 3H); 1.20(d, 6H). |
| 1.12 | H | 3-methyl-5-isopropylphenyl | 8.55(s, 1H); 7.65(s, 1H); 6.70–6.90(m, 3H); 3.95(s, 3H); 3.95 (s, 3H); 280–2.90(m, 1H); 2.55 (s, 3H); 2.35(s, 3H); 2.20 (s, 6H). |
| 1.13 | CH₃ | 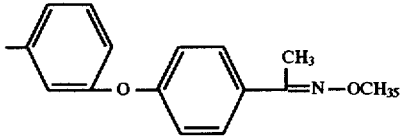 | oil; 7.01–7.61(m, 5H); 5.99–6.18 (m, 2H); 5.19–5.39(2d, 2H); 4.71 (d, 1H); 3.90(s, 3H); 3.70 (s, 3H); 2.58(s, 3H); 2.48 (s, 3H); 2.24(s, 3H). |
| 1.14 | CH₃ | 3-trifluoromethylphenyl | |
| 1.15 | CH₃ | 3-phenoxybenzyl | |
| 1.16 | CH₃ | 3-(2-cyanophenoxy)-phenyl | m.p. 144° C.; 6.78–7.69(m, 8H); 3.85(s, 3H); 3.68(s, 3H); 2.52 (s, 3H); 2,48(s, 3H). |
| 1.17 | CH₃ | 3-isopropylphenyl | 7.60(s, 1H); 6.85–7.30(m, 4H); 3.90(s, 3H); 3.79(s, 3H); 2.85–2.95(m, 1H); 2.55(s, 3H); 2.45 (s, 3H); 2.20(d, 6H). |
| 1.18 | CH₃ | phenyl | 7.60(s, 1H); 7.00–7.40(m, 5H); 3.91(5.3H); 3.72(s, 3H); 2.55 (s, 3H); 2.50(s, 3H). |
| 1.19 | CH₃ | 3-(3,5-dimethylphenoxy)-phenyl | |
| 1.20 | CH₃ | 3-(2-chloro-4-methylphenoxy)-phenyl | |
| 1.21 | CH₃ | 3-(4-chloro-2-methylphenoxy)-phenyl | |
| 1.22 | CH₃ | 3-(3-cyanophenoxy)-phenyl | |
| 1.23 | CH₃ | 3-(4-cyanophenoxy)-phenyl | |
| 1.24 | CH₃ | 3-(2-trifluoromethyl-phenoxy)-phenyl | |
| 1.25 | CH₃ | 3-(3-trifluoromethyl-phenoxy)-phenyl | |
| 1.26 | CH₃ | 3-(4-trifluoromethyl-phenoxy)-phenyl | |
| 1.27 | CH₃ | 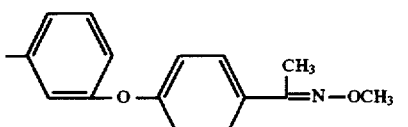 | |
| 1.28 | H |  | |
| 1.29 | CH₃ | 3-(3-chlorophenoxy)-phenyl | |

TABLE 1-continued

[Structure: pyrimidine with R2 and O-R3 substituents, bearing -C(=CH-OCH3)-C(COOCH3)=N-S-CH3 side chain]

| Comp. No. | R₂ | R₃ | physical data ¹H-NMR (CDCl₃) or/and m.p. |
|---|---|---|---|
| 1.30 | CH₃ | 3-(3-methoxyphenoxy)-phenyl | |
| 1.31 | CH₃ | 3-(2-methylphenoxy)-phenyl | 7.55(s, 1H); 6.58–7.30(m, 8H); 3.84(s, 3H); 3.65(s, 3H); 2.52 (s, 3H); 2.46(s, 3H); 2.22 (s, 3H). |
| 1.32 | CH₃ | 3-(2,5-dimethylphenoxy)-phenyl | |
| 1.33 | CH₃ | 3-(2,3-dimethylphenoxy)-phenyl | |
| 1.34 | CH₃ | 3-(3-methylphenoxy)-phenyl | |
| 1.35 | CH₃ | 3-benzyloxy-phenyl | |
| 1.36 | CH₃ | 3-(2-methylbenzyloxy)-phenyl | |
| 1.37 | CH₃ | 3-(2-chlorobenzyloxy)-phenyl | |
| 1.38 | CH₃ | 3-(2,5-dimethylbenzyloxy)-phenyl | |
| 1.39 | CH₃ | 3-(3-chlorobenzyloxy)-phenyl | 7.56(s, 1H); 6.40–7.46(m, 8H); 5.00(s, 2H); 3.86(s, 3H); 3.70 (s, 3H); 2.52(s, 3H); 2.48 (s, 3H). |
| 1.40 | CH₃ | 3-(3-methylbenzyloxy)-phenyl | |
| 1.41 | CH₃ | 3-(4-chlorobenzyloxy)-phenyl | |
| 1.42 | CH₃ | 3-(3-methoxybenzyloxy)-phenyl | |
| 1.43 | CH₃ | 3-(2-cyanobenzyloxy)-phenyl | |
| 1.44 | CH₃ | 3-(phenylethoxy)-phenyl | |
| 1.45 | CH₃ | 3-(phenoxy-methyl)-phenyl | |
| 1.46 | CH₃ | phenyl-CH₂-O-N=C(CH₃)-phenyl | |
| 1.47 | CH₃ | 3-(2,5-dimethylphenoxy-methyl)-phenyl | |
| 1.48 | CH₃ | phenyl-CH₂-O-phenyl-C(CH₃)=N-OCH₃ | |
| 1.49 | CH₃ | phenyl-CH₂-O-phenyl-C(CH₃)=N-O-allyl | |
| 1.50 | CH₃ | phenyl-C(CH₃)=N-O-(3-chlorobenzyl) | oil; 7.01–7.61(m, 9H); 5.20 (s, 2H); 3.86(s, 3H); 3.70 (s, 3H); 2.55(s, 3H); 2.45 (s, 3H); 2.25(s, 3H). |
| 1.51 | CH₃ | phenyl-C(CH₃)=N-O-(2,5-dichlorobenzyl) | |
| 1.52 | CH₃ | phenyl-C(CH₃)=N-O-(2,5-dimethylbenzyl) | |
| 1.53 | CH₃ | phenyl-C(CH₃)=N-O-(2-chlorobenzyl) | |

TABLE 1-continued
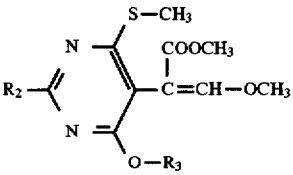
| Comp. No. | R₂ | R₃ | physical data ¹H-NMR (CDCl₃) or/and m.p. |
|---|---|---|---|
| 1.54 | CH₃ | 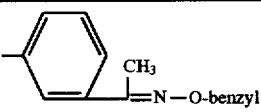 | |
| 1.55 | CH₃ | 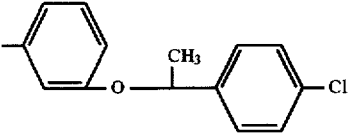 | |
| 1.56 | CH₃ | 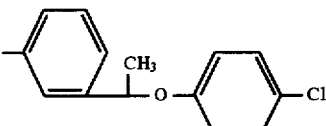 | |
| 1.57 | CH₃ | 3-(2-naphthyl)-phenyl | 7.20–7.85(m, 8H); 3.95(s, 3H); 3.70(s, 3H); 3.55(s, 3H); 3.45 (s, 3H); 2.55(s, 3H); 2.45 (s, 3H). |
| 1.58 | CH₃ | 3-(4-methylphenyl)-phenyl | |
| 1.59 | CH₃ | 3-(2-pyridyl)-phenyl | |
| 1.60 | CH₃ | 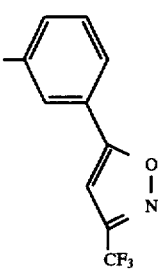 | 7.18–7.66(m, 5H); 6.98(s, 1H); 3.92(s, 3H); 3.70(s, 3H); 2.52 (s, 3H); 2.48(s, 3H). |
| 1.61 | H | 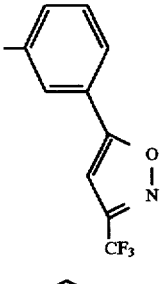 | 7.18–7.66(m, 5H); 6.98(s, 1H); 3.92(s, 3H); 3.70(s, 3H); 2.52 (s, 3H); 2.48(s, 3H)- |
| 1.62 | CH₃ | 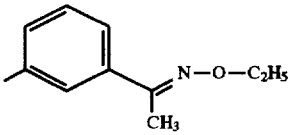 | oil; 7.60(s, 1H); 7.00–7.49(m, 4H); 4.22(8, 2H); 3.92(s, 3H); 3.82(s, 3H); 2.55(s, 3H); 2.45 (s, 3H); 2.22(s, 3H); 1.30 (t, 3H). |
| 1.63 | H | 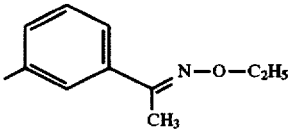 | 8.51(s, 1H); 7.42(s, 1H); 7.02– 7.52(m, 4H); 4.22(8, 2H); 3.90 (s, 3H); 3.86(s, 3H); 2.56 (s, 3H); 2.20(s, 3H); 1.28 (t, 3H). |

TABLE 1-continued

[Structure: R2 group attached to pyrimidine with S-CH3, COOCH3, C=CH-OCH3, and O-R3 substituents]

| Comp. No. | R2 | R3 | physical data<br>¹H-NMR (CDCl₃) or/and m.p. |
|---|---|---|---|
| 1.64 | CH₃ | [3-methylphenyl-isoxazole with CH₃] | |
| 1.65 | H | [3-methylphenyl-isoxazole with CH₃] | |
| 1.66 | CH₃ | [3-methylphenyl-isoxazole with C₂H₅] | 7.25–7.62(m, 3H); 7.70(d, 1H);<br>6.35(s, 1H); 3.90(s, 3H); 3.72<br>(s, 3H); 2.70(8, 2H); 2.55<br>(s, 3H); 2.48(s, 3H); 2.48<br>(s, 3H); 1.30(t, 3H). |
| 1.67 | H | [3-methylphenyl-isoxazole with C₂H₅] | |
| 1.68 | CH₃ | [3-methylphenyl-O-C(=N-)-S-benzo structure] | |
| 1.69 | CH₃ | [3-methylphenyl-benzothiazole] | |
| 1.70 | CH₃ | 3-methoxyphenyl | 7.58(s, 1H); 7.16–7.28 and<br>6.55–6.75(m, 4H); 3.89(s, 3H);<br>3.75(s, 3H); 3.75(s, 3H);<br>3.70(s, 3H); 2.52(s, 3H);<br>2.48(s, 3H). |
| 1.71 | CH₃ | [4-methylphenyl-isoxazole with C₃H₇-n] | |

TABLE 1-continued
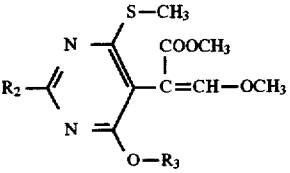
| Comp. No. | R₂ | R₃ | physical data ¹H-NMR (CDCl₃) or/and m.p. |
|---|---|---|---|
| 1.72 | CH₃ | 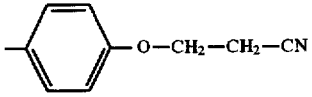 | |
| 1.73 | CH₃ | 3-(4-chlorophenyl)-phenyl | 7.61(s, 1H); 7.00–7.52(m, 8H); 3.90(s, 3H); 3.70(s, 3H); 2.55 (s, 3H); 2.45(s, 3H). |
| 1.74 | CH₃ | 3-(4-cyanophenyl)-phenyl | |
| 1.75 | CH₃ | 3-(3-cyanophenyl)-phenyl | 7.10–7.85(m, 9H); 3.50(s, 3H); 3.70(s, 3H); 2.55(s, 3H); 2.45 (s, 3H). |
| 1.76 | CH₃ | 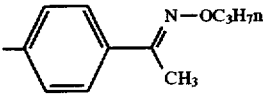 | 7.60(s, 1H), 7.00–7.42(m, 8H); 4.15(t, 2H), 3.90(s, 3H); 3.70 (s, 3H); 2.55(s, 3H); 2.48(s, 3H); 2.20(s, 3H); 1.79(m, 2H); 1.00(t, 3H). |
| 1.77 | CH₃ | 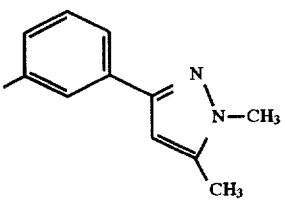 | |
| 1.78 | CH₃ | 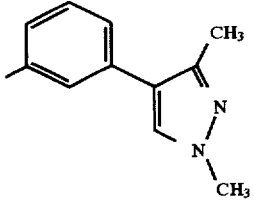 | |
| 1.79 | CH₃ | 3-(2-cyanophenyl)-phenyl | 7.10–7.80(m, 9H); 3.50(s, 3H); 3.70(s, 3H); 2.52(s, 3H); 2.18 (s, 3H). |
| 1.80 | CH₃ | 3-(2-methylphenyl)-phenyl | 7.00–7.60(m, 9H); 3.91(s, 3H); 3.70(s, 3H); 3.55(s, 3H); 3.50 (s, 3H); 2.30(s, 3H). |
| 1.81 | CH₃ | 3,5-dimethylphenyl | 7.60(s, 1H); 6.62–6.80(m, 3H); 3.95(s, 3H); 3.75(s, 3H), 2.52 (s, 3H); 2.48(s, 3H); 2.30 (s, 6H) |

TABLE 2

Structure: pyrimidine with R₂, substituents S-CH₃, COOCH₃, C=N-OCH₃, O-R₃

| Comp. No. | R₂ | R₃ | physical data ¹H-NMR or/and m.p. |
|---|---|---|---|
| 2.01 | CH₃ | 3-biphenylyl | |
| 2.02 | H | 3-biphenylyl | |
| 2.03 | H | 3-trifluoromethylphenyl | |
| 2.04 | CH₃ | 3-trifluoromethylphenyl | |
| 2.05 | CH₃ | 3-phenoxyphenyl | |
| 2.06 | CH₃ | 3-chlorophenyl | |
| 2.07 | H | 3-trifluoromethoxyphenyl | |
| 2.08 | H | 3-phenoxyphenyl | |
| 2.09 | H | 3-chlorophenyl | |
| 2.10 | CH₃ | 3-tert.butylphenyl | |
| 2.11 | CH₃ | 3-methylphenyl | |
| 2.12 | CH₃ | phenyl-C(CH₃)=N-OCH₃ | |
| 2.13 | CH₃ | 3-methyl-5-isopropylphenyl | |
| 2.14 | H | 3-methyl-5-isopropylphenyl | |
| 2.15 | CH₃ | phenyl-C(CH₃)=N-O-allyl | |
| 2.16 | CH₃ | 3-trifluoromethylbenzyl | |
| 2.17 | CH₃ | 3-phenoxybenzyl | |
| 2.18 | CH₃ | 3-(2-cyanophenoxy)-phenyl | m.p. 126° C.; 6.78–7.69(m, 8H); 4.12(s, 3H); 3.86(s, 3H); 2.57 (s, 3H); 2.50(s, 3H) |
| 2.19 | CH₃ | 3-isopropylphenyl | |
| 2.20 | CH₃ | phenyl | |
| 2.21 | CH₃ | 3-(3,5-dimethylphenoxy)-phenyl | |
| 2.22 | CH₃ | 3-(2-chloro-4-methylphenoxy)-phenyl | |
| 2.23 | CH₃ | 3-(4-chloro-2-methylphenoxy)-phenyl | |
| 2.24 | CH₃ | 3-(3-cyanophenoxy)-phenyl | |
| 2.25 | CH₃ | 3-(4-cyanophenoxy)-phenyl | |
| 2.26 | CH₃ | 3-(2-trifluoromethyl-phenoxy)-phenyl | |
| 2.27 | CH₃ | 3-(3-trifluoromethyl-phenoxy)-phenyl | |
| 2.28 | CH₃ | 3-(4-trifluoromethyl-phenoxy)-phenyl | |
| 2.29 | CH₃ | phenyl-O-phenyl-C(CH₃)=N-OCH₃ | |
| 2.30 | CH₃ | phenyl-O-phenyl-C(CH₃)=N-OCH₃ (ethyl variant) | 7.00–7.55(m, 4H); 4.22(, 2H); 3.78(S, 3H); 2.52(s, 3H); 2.48 (s, 3H); 2.26(s, 3H); 1.32 (t, 3H). |
| 2.31 | CH₃ | 3-(3-chlorophenoxy)-phenyl | |
| 2.32 | CH₃ | 3-(3-methoxyphenoxy)-phenyl | |
| 2.33 | CH₃ | 3-(2-methylphenoxy)-phenyl | |
| 2.34 | CH₃ | 3-(2,5-dimethylphenoxy)-phenyl | |
| 2.35 | CH₃ | 3-(3-methylphenoxy)-phenyl | |
| 2.36 | CH₃ | 3-benzyloxy-phenyl | |
| 2.37 | CH₃ | 3-(2-methylbenzyloxy)-phenyl | |
| 2.38 | CH₃ | 3-(2-chlorobenzyloxy)-phenyl | |
| 2.39 | CH₃ | 3-(2,5-dichlorobenzyloxy)-phenyl | |
| 2.40 | CH₃ | 3-(2,5-dimethylbenzyloxy)-phenyl | |

TABLE 2-continued

Structure:
R$_2$-C(=N)-N=C(S-CH$_3$)-C(COOCH$_3$)(C=N-OCH$_3$)-C(O-R$_3$)=N (pyrimidine ring)

| Comp. No. | R$_2$ | R$_3$ | physical data $^1$H-NMR or/and m.p. |
|---|---|---|---|
| 2.41 | CH$_3$ | 3-(3-chlorobenzyloxy)-phenyl | 6.40–7.42(m, 8H); 5.02(s, 2H); 4.12(s, 3H); 3.85(s, 3H); 2.58 (s, 3H); 2.45(s, 3H) |
| 2.42 | CH$_3$ | 3-(3-methylbenzyloxy)-phenyl | |
| 2.43 | CH$_3$ | 3-(3-chloro-4-methylbenzyloxy)-phenyl | |
| 2.44 | CH$_3$ | 3-(3-methoxybenzyloxy)-phenyl | |
| 2.45 | CH$_3$ | 3-(2-cyanobenzyloxy)-phenyl | |
| 2.46 | CH$_3$ | 3-(2-nitrobenzyloxy)-phenyl | |
| 2.47 | CH$_3$ | 3-(phenylethoxy)-phenyl | |
| 2.48 | CH$_3$ | 3-(phenoxy-methyl)-phenyl | |
| 2.49 | CH$_3$ | 3-(3-chlorophenoxymethyl)-phenyl | |
| 2.50 | CH$_3$ | 4-[CH$_2$-O-N=C(CH$_3$)-phenyl]-phenyl | |
| 2.51 | CH$_3$ | 3-(2,5-dimethylphenoxy-methyl)-phenyl | |
| 2.52 | CH$_3$ | 4-[CH$_2$-O-(3-{C(CH$_3$)=N-OCH$_3$}phenyl)]-phenyl | |
| 2.53 | CH$_3$ | 4-[C(CH$_3$)=N-O-(2,5-dimethylbenzyl)]-phenyl | |
| 2.54 | CH$_3$ | 4-[C(CH$_3$)=N-O-(2-chlorobenzyl)]-phenyl | 7.00–7.52(m, 8H); 5.18(s, 2H); 4.14(s, 3H); 3.75(s, 3H); 2.56 (s, 3H); 2.45(s, 3H); 2.25 (s, 3H) |
| 2.55 | CH$_3$ | 4-[C(CH$_3$)=N-O-benzyl]-phenyl | |
| 2.56 | CH$_3$ | 3-(2-naphthyl)-phenyl | |
| 2.57 | CH$_3$ | 3-methoxyphenyl | |
| 2.58 | CH$_3$ | 4-[5-isoxazolyl with CF$_3$]-phenyl | |
| 2.59 | CH$_3$ | 4-[5-isoxazolyl with CH$_3$]-phenyl | |
| 2.60 | CH$_3$ | 4-[5-isoxazolyl with C$_2$H$_5$]-phenyl | |

TABLE 2-continued

[Structure: R₂-substituted pyrimidine with S-CH₃, C(COOCH₃)=N-OCH₃, and O-R₃ groups]

| Comp. No. | R₂ | R₃ | physical data ¹H-NMR or/and m.p. |
|---|---|---|---|
| 2.61 | CH₃ | 4-(5-n-propyl-isoxazol-3-yl-vinyl)phenyl | |
| 2.62 | CH₃ | 4-(benzothiazol-2-yloxy)phenyl | |
| 2.63 | CH₃ | 4-(benzothiazol-2-yloxy)phenyl | |
| 2.64 | CH₃ | 4-(2-cyanoethoxy)phenyl | |

TABLE 3

[Structure: R₂-substituted pyrimidine with S-CH₃, C(COOCH₃)=CH-OH, and O-R₃ groups]

| Comp. No. | R₂ | R₃ | physical data |
|---|---|---|---|
| 3.01 | CH₃ | 3-biphenylyl | |
| 3.02 | H | 3-biphenylyl | |
| 3.03 | H | 3-trifluoromethylphenyl | |
| 3.04 | CH₃ | 3-trifluoromethylphenyl | Rf = 0.60 (30% ethyl acetate in hexane) |
| 3.05 | CH₃ | 3-phenoxyphenyl | |
| 3.06 | CH₃ | 3-chlorophenyl | |
| 3.07 | H | 3-phenoxyphenyl | |
| 3.08 | CH₃ | 3-tert.butylphenyl | Rf = 0.78 (30% ethyl acetate in hexane) |
| 3.09 | CH₃ | 3-methylphenyl | |
| 3.10 | CH₃ | 3-(1-methoxyimino-ethyl)phenyl | |
| 3.11 | CH₃ | 3-methyl-5-isopropylphenyl | Rf = 0.75 (30% ethyl acetate in hexane) |
| 3.12 | H | 3-methyl-5-isopropylphenyl | |
| 3.13 | CH₃ | 3-(1-allyloxyimino-ethyl)phenyl | |
| 3.14 | CH₃ | 3-trifluoromethylbenzyl | |
| 3.15 | CH₃ | 3-phenoxybenzyl | |
| 3.16 | CH₃ | 3-(2-cyanophenoxy)-phenyl | Rf = 0.55–0.60 (30% ethyl acetate in hexane) |
| 3.17 | CH₃ | 3-isopropylphenyl | |
| 3.18 | CH₃ | phenyl | |

TABLE 3-continued

Structure: Pyrimidine ring with R₂ at one position, substituents S—CH₃, and C=CH—OH with COOCH₃; O—R₃ group.

| Comp. No. | R₂ | R₃ | physical data |
|---|---|---|---|
| 3.19 | CH₃ | 3-(3,5-dimethylphenoxy)-phenyl | |
| 3.20 | CH₃ | 3-(2-chloro-4-methylphenoxy)-phenyl | |
| 3.21 | CH₃ | 3-(4-chloro-2-methylphenoxy)-phenyl | |
| 3.22 | CH₃ | 3-(3-cyanophenoxy)-phenyl | |
| 3.23 | CH₃ | 3-(4-cyanophenoxy)-phenyl | |
| 3.24 | CH₃ | 3-(2-trifluoromethyl-phenoxy)-phenyl | |
| 3.25 | CH₃ | 3-(3-trifluoromethyl-phenoxy)-phenyl | |
| 3.26 | CH₃ | 3-(4-trifluoromethyl-phenoxy)-phenyl | |
| 3.27 | CH₃ | phenyl-C(CH₃)=N—OCH₃ | |
| 3.28 | H | phenyl-O-phenyl-C(CH₃)=N—OCH₃ | |
| 3.29 | CH₃ | 3-(3-chlorophenoxy)-phenyl | |
| 3.30 | CH₃ | 3-(3-methoxyphenoxy)-phenyl | |
| 3.31 | CH₃ | 3-(2-methylphenoxy)-phenyl | Rf = 0.56 (30% ethyl acetate in hexane) |
| 3.32 | CH₃ | 3-(2,5-dimethylphenoxy)-phenyl | |
| 3.33 | CH₃ | 3-(2,3-dimethylphenoxy)-phenyl | |
| 3.34 | CH₃ | 3-(3-methylphenoxy)-phenyl | |
| 3.35 | CH₃ | 3-benzyloxy-phenyl | |
| 3.36 | CH₃ | 3-(2-methylbenzyloxy)-phenyl | |
| 3.37 | CH₃ | 3-(2-chlorobenzyloxy)-phenyl | |
| 3.38 | CH₃ | 3-(2,5-dimethylbenzyloxy)-phenyl | |
| 3.39 | CH₃ | 3-(3-chlorobenzyloxy)-phenyl | |
| 3.40 | CH₃ | 3-(3-methylbenzyloxy)-phenyl | |
| 3.41 | CH₃ | 3-(4-chlorobenzyloxy)-phenyl | |
| 3.42 | CH₃ | 3-(3-methoxybenzyloxy)-phenyl | |
| 3.43 | CH₃ | 3-(2-cyanobenzyloxy)-phenyl | |
| 3.44 | CH₃ | 3-(phenylethoxy)-phenyl | |
| 3.45 | CH₃ | 3-(phenoxy-methyl)-phenyl | |
| 3.46 | CH₃ | phenyl-CH₃—O—N=C(CH₃)—phenyl | |
| 3.47 | CH₃ | 3-(2,5-dimethylphenoxy-methyl)-phenyl | |
| 3.48 | CH₃ | phenyl-CH₂—O-phenyl-C(CH₃)=N—OCH₃ | |
| 3.49 | CH₃ | phenyl-CH₂—O-phenyl-C(CH₃)=N—O-allyl | |
| 3.50 | CH₃ | phenyl-C(CH₃)=N—O-(3-chlorobenzyl) | |

TABLE 3-continued

[Structure: pyrimidine with S-CH₃, N, COOCH₃, C=CH-OH, R₂, N, O-R₃ substituents]

| Comp. No. | R₂ | R₃ | physical data |
|---|---|---|---|
| 3.51 | CH₃ | phenyl-C(CH₃)=N-O-(2,5-dichlorobenzyl) | |
| 3.52 | CH₃ | phenyl-C(CH₃)=N-O-(2,5-dimethylbenzyl) | |
| 3.53 | CH₃ | phenyl-C(CH₃)=N-O-(2-chlorobenzyl) | |
| 3.54 | CH₃ | phenyl-C(CH₃)=N-O-benzyl | |
| 3.55 | CH₃ | phenyl-O-CH(CH₃)-(4-chlorophenyl) | |
| 3.56 | CH₃ | phenyl-CH(CH₃)-O-(4-chlorophenyl) | |
| 3.57 | CH₃ | 3-(2-naphthyl)-phenyl | |
| 3.58 | CH₃ | 3-(4-methylphenyl)-phenyl | |
| 3.59 | CH₃ | 3-(2-pyridyl)-phenyl | |
| 3.60 | CH₃ | phenyl-isoxazole-CF₃ | |
| 3.61 | H | phenyl-isoxazole-CF₃ | |

TABLE 3-continued
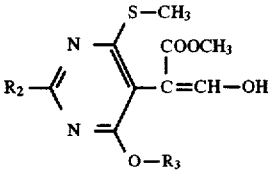
| Comp. No. | R₂ | R₃ | physical data |
|---|---|---|---|
| 3.62 | CH₃ | 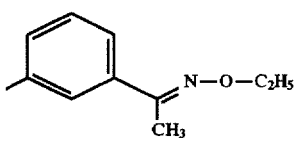 | |
| 3.63 | CH₃ | 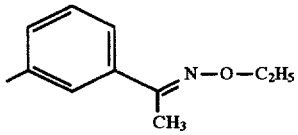 | |
| 3.64 | CH₃ | 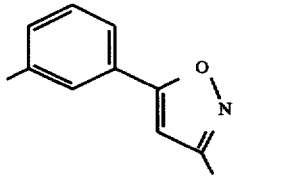 | |
| 3.65 | H | 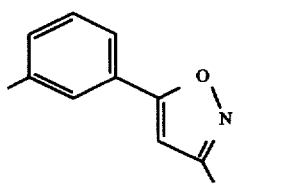 | |
| 3.66 | CH₃ | 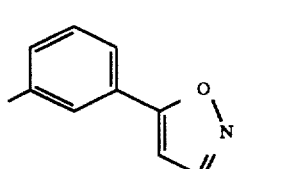 | |
| 3.67 | H | 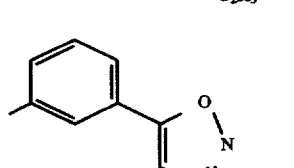 | |
| 3.68 | CH₃ | 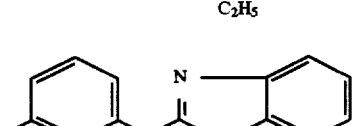 | |

TABLE 3-continued

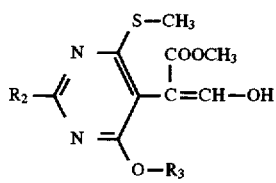

| Comp. No. | R$_2$ | R$_3$ | physical data |
|---|---|---|---|
| 3.69 | CH$_3$ | [3-methylphenyl-C(=N-2-phenyl)-S-] | |
| 3.70 | CH$_3$ | 3-methoxyphenyl | Rf = 0.55 (30% ethyl acetate in hexane) |
| 3.71 | CH$_3$ | [4-(3-n-propyl-isoxazol-5-yl)phenyl] | |
| 3.72 | CH$_3$ | [4-(2-cyanoethoxy)phenyl] | |
| 2.73 | CH$_3$ | 3-(4-chlorophenyl)phenyl | |
| 3.74 | CH$_3$ | 3-(4-cyanophenyl)phenyl | |
| 3.75 | CH$_3$ | 3-(3-cyanophenyl)phenyl | |
| 3.76 | CH$_3$ | [4-(1-(n-propoxyimino)ethyl)phenyl] | |
| 3.77 | CH$_3$ | [3-(1-methyl-5-methyl-pyrazol-3-yl)phenyl] | |
| 3.78 | CH$_3$ | [3-(1,3-dimethyl-pyrazol-4-yl)phenyl] | |
| 3.79 | CH$_3$ | 3-(2-cyanophenyl)phenyl | |
| 3.80 | CH$_3$ | 3-(2-methylphenyl)phenyl | |
| 3.81 | CH$_3$ | 3,5-dimethylphenyl | |

TABLE 4

Structure:
$R_2$—(pyrimidine with S—CH$_3$ and O—R$_3$ substituents)—C(=CH—OH)—COOCH$_3$

| Comp. No. | R$_2$ | R$_3$ | physical data $^1$H-NMR (CDCl$_3$) or/and m.p. |
|---|---|---|---|
| 4.01 | CH$_3$ | 3-biphenylyl | |
| 4.02 | H | 3-biphenylyl | |
| 4.03 | H | 3-trifluoromethylphenyl | |
| 4.04 | CH$_3$ | 3-trifluoromethylphenyl | |
| 4.05 | CH$_3$ | 3-phenoxyphenyl | |
| 4.06 | CH$_3$ | 3-chlorophenyl | |
| 4.07 | H | 3-trifluoromethoxyphenyl | |
| 4.08 | H | 3-phenoxyphenyl | |
| 4.09 | H | 3-chlorophenyl | |
| 4.10 | CH$_3$ | 3-tert.butylphenyl | |
| 4.11 | CH$_3$ | 3-methylphenyl | |
| 4.12 | CH$_3$ | 4-[C(CH$_3$)=N—OCH$_3$]-phenyl | |
| 4.13 | CH$_3$ | 3-methyl-5-isopropylphenyl | |
| 4.14 | H | 3-methyl-5-isopropylphenyl | |
| 4.15 | CH$_3$ | 4-[C(CH$_3$)=N—O-allyl]-phenyl | |
| 4.16 | CH$_3$ | 3-trifluoromethylbenzyl | |
| 4.17 | CH$_3$ | 3-phenoxybenzyl | |
| 4.18 | CH$_3$ | 3-(2-cyanophenoxy)-phenyl | |
| 4.19 | CH$_3$ | 3-isopropylphenyl | |
| 4.20 | CH$_3$ | phenyl | |
| 4.21 | CH$_3$ | 3-(3,5-dimethylphenoxy)-phenyl | |
| 4.22 | CH$_3$ | 3-(2-chloro-4-methylphenoxy)-phenyl | |
| 4.23 | CH$_3$ | 3-(4-chloro-2-methylphenoxy)-phenyl | |
| 4.24 | CH$_3$ | 3-(3-cyanophenoxy)-phenyl | |
| 4.25 | CH$_3$ | 3-(4-cyanophenoxy)-phenyl | |
| 4.26 | CH$_3$ | 3-(2-trifluoromethyl-phenoxy)-phenyl | |
| 4.27 | CH$_3$ | 3-(3-trifluoromethyl-phenoxy)-phenyl | |
| 4.28 | CH$_3$ | 3-(4-fluoromethyl-phenoxy)-phenyl | |
| 4.29 | CH$_3$ | 4-[O-C$_6$H$_4$-C(CH$_3$)=N—OCH$_3$]-phenyl | |
| 4.30 | CH$_3$ | 4-[O-C$_6$H$_4$-C(CH$_3$)=N—OCH$_3$]-phenyl | |
| 4.31 | CH$_3$ | 3-(3-chlorophenoxy)-phenyl | |
| 4.32 | CH$_3$ | 3-(3-methoxyphenoxy)-phenyl | |
| 4.33 | CH$_3$ | 3-(2-methylphenoxy)-phenyl | |
| 4.34 | CH$_3$ | 3-(2,5-dimethylphenoxy)-phenyl | |
| 4.35 | CH$_3$ | 3-(3-methylphenoxy)-phenyl | |
| 4.36 | CH$_3$ | 3-benzyloxy-phenyl | |
| 4.37 | CH$_3$ | 3-(2-methylbenzyloxy)-phenyl | |
| 4.38 | CH$_3$ | 3-(2-chlorobenzyloxy)-phenyl | |
| 4.39 | CH$_3$ | 3-(2,5-dichlorobenzyloxy)-phenyl | |
| 4.40 | CH$_3$ | 3-(2,5-dimethylbenzyloxy)-phenyl | |
| 4.41 | CH$_3$ | 3-(3-chlorobenzyloxy)-phenyl | |
| 4.42 | CH$_3$ | 3-(3-methylbenzyloxy)-phenyl | |

TABLE 4-continued

[Structure: R_2-C(=N)-C(=N)-... with substituents S-CH_3, COOCH_3, C=CH-OH, O-R_3]

| Comp. No. | R_2 | R_3 | physical data $^1$H-NMR (CDCl$_3$) or/and m.p. |
|---|---|---|---|
| 4.43 | CH_3 | 3-(3-chloro-4-methylbenzyloxy)-phenyl | |
| 4.44 | CH_3 | 3-(3-methoxybenzyloxy)-phenyl | |
| 4.45 | CH_3 | 3-(2-cyanobenzyloxy)-phenyl | |
| 4.46 | CH_3 | 3-(2-nitrobenzyloxy)-phenyl | |
| 4.47 | CH_3 | 3-(phenylethoxy)-phenyl | |
| 4.48 | CH_3 | 3-(phenoxy-methyl)-phenyl | |
| 4.49 | CH_3 | 3-(3-chlorophenoxymethyl)-phenyl | |
| 4.50 | CH_3 | –phenyl–CH_2–O–N=C(CH_3)–phenyl | |
| 4.51 | CH_3 | 3-(2,5-dimethylphenoxy-methyl)-phenyl | |
| 4.52 | CH_3 | –phenyl–CH_2–O–phenyl–C(CH_3)=N–OCH_3 | |
| 4.53 | CH_3 | –phenyl–C(CH_3)=N–O-(2,5-dimethylbenzyl) | |
| 4.54 | CH_3 | –phenyl–C(CH_3)=N–O-(2-chlorobenzyl) | |
| 4.55 | CH_3 | –phenyl–C(CH_3)=N–O-benzyl | |
| 4.56 | CH_3 | 3-(2-naphthyl)-phenyl | |
| 4.57 | CH_3 | 3-methoxyphenyl | |
| 4.58 | CH_3 | | |
| 4.59 | CH_3 | –phenyl–CH=CH–C(CH_3)=N–O (isoxazole) | |
| 4.60 | CH_3 | –phenyl–CH=CH–C(C_2H_5)=N–O (isoxazole) | |
| 4.61 | CH_3 | –phenyl–CH=CH–C(C_3H_7-n)=N–O (isoxazole) | |
| 4.62 | CH_3 | –phenyl–O-(benzothiazol-2-yl) | |

TABLE 4-continued

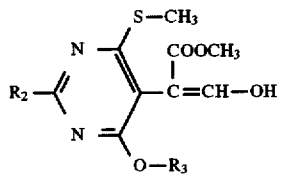

| Comp. No. | R₂ | R₃ | physical data ¹H-NMR (CDCl₃) or/and m.p. |
|---|---|---|---|
| 4.63 | CH₃ | (4-(benzothiazol-2-yloxy)phenyl) | |
| 4.64 | CH₃ | (4-(2-cyanoethoxy)phenyl) | 4 |

TABLE 5

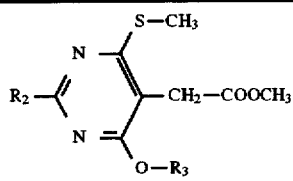

| Comp. No. | R₂ | R₃ | physical data ¹H-NMR (CDCl₃) or/and m.p. |
|---|---|---|---|
| 5.01 | CH₃ | 3-biphenylyl | |
| 5.02 | H | 3-biphenylyl | |
| 5.03 | H | 3-trifluoromethylphenyl | |
| 5.04 | CH₃ | 3-trifluoromethylphenyl | 7.25–7.55(m, 4H); 3.78(s, 3H); 3.70(s, 3H); 2.62(s, 3H); 2.46(s, 3H). |
| 5.05 | CH₃ | 3-phenoxyphenyl | |
| 5.06 | CH₃ | 3-chlorophenyl | |
| 5.07 | H | 3-phenoxyphenyl | |
| 5.08 | CH₃ | 3-tert.butylphenyl | 6.88–7.30(m, 4H); 3.78(s, 2H); 3.69(s, 3H); 2.59(s, 3H); 2.44(s, 3H); 1.28(s, 9H). |
| 5.09 | CH₃ | 3-methylphenyl | |
| 5.10 | CH₃ | 4-(C(CH₃)=N-OCH₃)phenyl | |
| 5.11 | CH₃ | 3-methyl-5-isopropylphenyl | 6.18–6.84(m, 3H); 3.74(s, 2H); 3.69(s, 3H); 2.85(m, 1H); 2.51(s, 3H); 2.45(s, 3H); 2.34(s, 3H); 1.22(d, 6H). |
| 5.12 | H | 3-methyl-5-isopropylphenyl | |
| 5.13 | CH₃ | 4-(C(CH₃)=N-O-allyl)phenyl | |
| 5.14 | CH₃ | 3-trifluoromethylbenzyl | |
| 5.15 | CH₃ | 3-phenoxybenzyl | |
| 5.16 | CH₃ | 3-(2-cyanophenoxy)-phenyl | 6.78–7.70(m, 8H); 3.86(s, 3H); 3.68(s, 3H); 2.52(s, 3H); 2.48(s, 3H). |
| 5.17 | CH₃ | 3-isopropylphenyl | |
| 5.18 | CH₃ | phenyl | |
| 5.19 | CH₃ | 3-(3,5-dimethylphenoxy)-phenyl | |
| 5.20 | CH₃ | 3-(2-chloro-4-methylphenoxy)-phenyl | |
| 5.21 | CH₃ | 3-(4-chloro-2-methylphenoxy)-phenyl | |
| 5.22 | CH₃ | 3-(3-cyanophenoxy)-phenyl | |
| 5.23 | CH₃ | 3-(4-cyanophenoxy)-phenyl | |
| 5.24 | CH₃ | 3-(2-trifluoromethyl-phenoxy)-phenyl | |

TABLE 5-continued

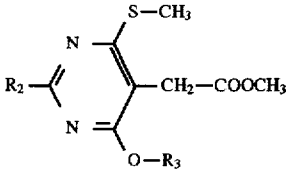

| Comp. No. | R₂ | R₃ | physical data ¹H-NMR (CDCl₃) or/and m.p. |
|---|---|---|---|
| 5.25 | CH₃ | 3-(3-trifluoromethyl-phenoxy)-phenyl | |
| 5.26 | CH₃ | 3-(4-trifluoromethyl-phenoxy)-phenyl | |
| 5.27 | CH₃ | 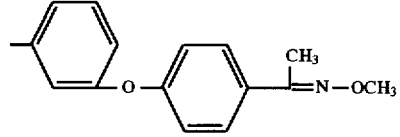 | |
| 5.28 | H | 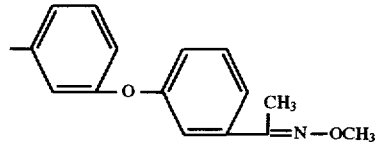 | |
| 5.29 | CH₃ | 3-(3-chlorophenoxy)-phenyl | |
| 5.30 | CH₃ | 3-(3-methoxyphenoxy)-phenyl | |
| 5.31 | CH₃ | 3-(2-methylphenoxy)-phenyl | 6.66–7.32(m, 8H); 3.71(s, 2H); 3.68(s, 3H); 2.58(s, 3H); 2.45(s, 3H); 2.27(s, 3H). |
| 5.32 | CH₃ | 3-(2,5-dimethylphenoxy)-phenyl | |
| 5.33 | CH₃ | 3-(2,3-dimethylphenoxy)-phenyl | |
| 5.34 | CH₃ | 3-(3-methylphenoxy)-phenyl | |
| 5.35 | CH₃ | 3-benzyloxy-phenyl | |
| 5.36 | CH₃ | 3-(2-methylbenzyloxy)-phenyl | |
| 5.37 | CH₃ | 3-(2-chlorobenzyloxy)-phenyl | |
| 5.38 | CH₃ | 3-(2,5-dimethylbenzyloxy)-phenyl | |
| 5.39 | CH₃ | 3-(3-chlorobenzyloxy)-phenyl | |
| 5.40 | CH₃ | 3-(3-methylbenzyloxy)-phenyl | |
| 5.41 | CH₃ | 3-(4-chlorobenzyloxy)-phenyl | |
| 5.42 | CH₃ | 3-(3-methoxybenzyloxy)-phenyl | |
| 5.43 | CH₃ | 3-(2-cyanobenzyloxy)-phenyl | |
| 5.44 | CH₃ | 3-(phenylethoxy)-phenyl | |
| 5.45 | CH₃ | 3-(phenoxy-methyl)-phenyl | |
| 5.46 | CH₃ | 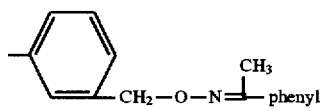 | |
| 5.47 | CH₃ | 3-(2,5-dimethylphenoxy-methyl)-phenyl | |
| 5.48 | CH₃ | 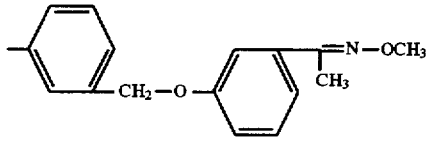 | |
| 5.49 | CH₃ | 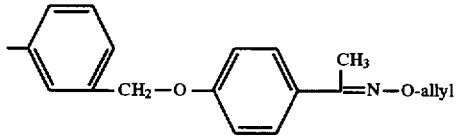 | |
| 5.50 | CH₃ | 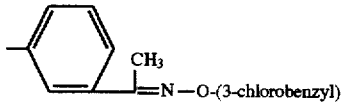 | |

TABLE 5-continued
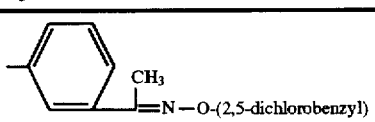
| Comp. No. | R₂ | R₃ | physical data ¹H-NMR (CDCl₃) or/and m.p. |
|---|---|---|---|
| 5.51 | CH₃ | 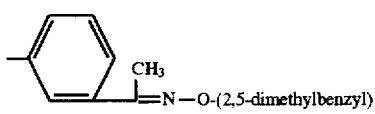 |  |
| 5.52 | CH₃ | 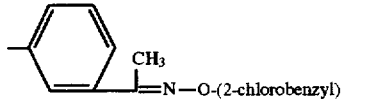 |  |
| 5.53 | CH₃ | 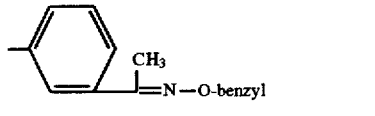 |  |
| 5.54 | CH₃ | 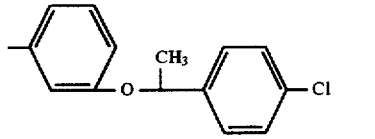 |  |
| 5.55 | CH₃ | 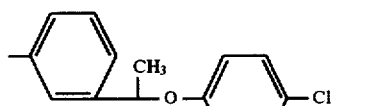 |  |
| 5.56 | CH₃ | 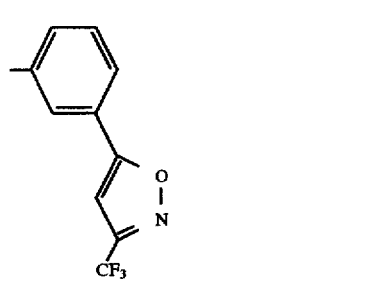 |  |
| 5.57 | CH₃ | 3-(2-naphthyl)-phenyl |  |
| 5.58 | CH₃ | 3-(4-methylphenyl)-phenyl |  |
| 5.59 | CH₃ | 3-(2-pyridyl)-phenyl |  |
| 5.60 | CH₃ | 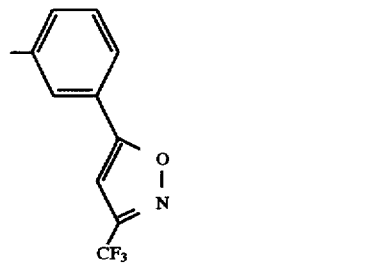 |  |
| 5.61 | H | 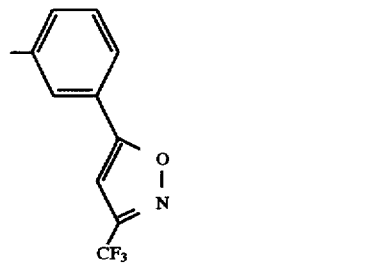 |  |

TABLE 5-continued
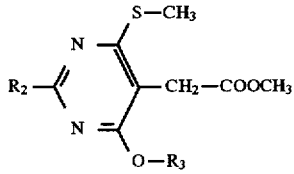
| Comp. No. | R₂ | R₃ | physical data $^1$H-NMR (CDCl$_3$) or/and m.p. |
|---|---|---|---|
| 5.62 | CH₃ | 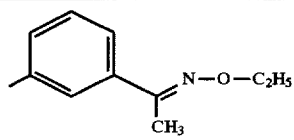 | |
| 5.63 | H | 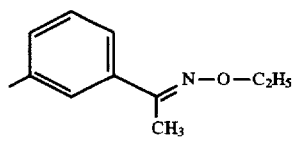 | |
| 5.64 | CH₃ | 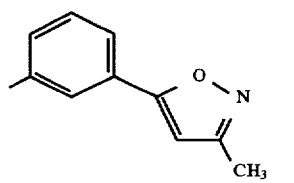 | |
| 5.65 | H | 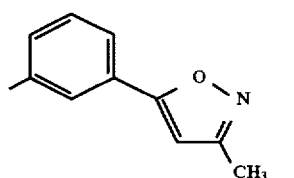 | |
| 5.66 | CH₃ | 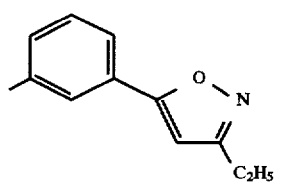 | |
| 5.67 | H | 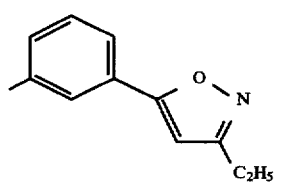 | |
| 5.68 | CH₃ | 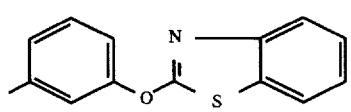 | |
| 5.69 | CH₃ | 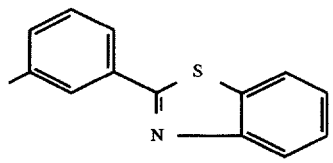 | |
| 5.70 | CH₃ | 3-methoxyphenyl | 6.62–6.78 and 7.20–7.30(m, 4H); 3.78(s, 3H); 3.75(s, 2H); 3.71(s, 3H); 2.58(s, 3H); 2.45(s, 3H) |

TABLE 5-continued

Structure: R₂ group attached to pyrimidine ring with S—CH₃, CH₂—COOCH₃, and O—R₃ substituents

| Comp. No. | R₂ | R₃ | physical data ¹H-NMR (CDCl₃) or/and m.p. |
|---|---|---|---|
| 5.71 | CH₃ | 4-(3-n-propylisoxazol-5-yl)phenyl | |
| 5.72 | CH₃ | 4-(2-cyanoethoxy)phenyl | |
| 5.73 | CH₃ | 3-(4-chlorophenyl)phenyl | |
| 5.74 | CH₃ | 3-(4-cyanophenyl)phenyl | |
| 5.75 | CH₃ | 3-(3-cyanophenyl)phenyl | |
| 5.76 | CH₃ | 4-[C(CH₃)=N—OC₃H₇n]phenyl | |
| 5.77 | CH₃ | 3-[CH=C(CH₃)—N(CH₃)—N=]phenyl (pyrazole-related) | |
| 5.78 | CH₃ | 3-(1,3-dimethylpyrazol-4-yl)phenyl | |
| 5.79 | CH₃ | 3-(2-cyanophenyl)phenyl | |
| 5.80 | CH₃ | 3-(2-methylphenyl)phenyl | |
| 5.81 | CH₃ | 3,5-dimethylphenyl | |

TABLE 6

Structure: R₂ group attached to pyrimidine ring with S—CH₃, CH₂—COOCH₃, and Cl substituents

| Comp. No. | R² | physical data |
|---|---|---|
| 6.01 | CH₃ | 3.80(s, 2H); 3.75(s, 3H); 2.62(s, 6H) |
| 6.02 | H | 8.50(s, 1H); 3.81(s, 2H); 3.76(s, 3H); 2.60(s, 3H) |
| 6.03 | C₂H₅ | |

TABLE 7

[Structure: pyrimidine ring with R₂ at 2-position, S-CH₃ at one position, O-R₃ at another, and substituent C(COOCH₃)=CH-N(CH₃)₂]

| Comp. No. | R₂ | R₃ | physical data ¹H-NMR (CDCl₃) or/and m.p. |
|---|---|---|---|
| 7.01 | CH₃ | 3-biphenylyl | |
| 7.02 | H | 3-biphenylyl | |
| 7.03 | H | 3-trifluoromethylphenyl | |
| 7.04 | CH₃ | 3-trifluoromethylphenyl | 7.70(s, 1H); 7.22–7.48(m, 4H); 3.60(s, 3H); 2.85(s, 6H); 2.49(d, 6H). |
| 7.05 | CH₃ | 3-phenoxyphenyl | |
| 7.06 | CH₃ | 3-chlorophenyl | |
| 7.07 | H | 3-phenoxyphenyl | |
| 7.08 | CH₃ | 3-tert.butylphenyl | 7.69(s, 1H); 7.08–7.30(m, 4H); 3.60(s, 3H); 2.85(s, 6H); 2.50(d, 6H); 1.30(s, 9H). |
| 7.09 | CH₃ | 3-methylphenyl | |
| 7.10 | CH₃ | [phenyl with C(CH₃)=N-OCH₃ substituent] | |
| 7.11 | CH₃ | 3-methyl-5-isopropylphenyl | 7.68(s, 1H); 6.68–6.82(3s, 1H each); 3.60 and 2.30(2s, 3H each); 2.85(s, 7H); 2.50(d, 6H); 1.20(d, 6H). |
| 7.12 | H | 3-methyl-5-isopropylphenyl | |
| 7.13 | CH₃ | [phenyl with C(CH₃)=N-O-allyl substituent] | |
| 7.14 | CH₃ | 3-trifluoromethylbenzyl | |
| 7.15 | CH₃ | 3-phenoxybenzyl | |
| 7.16 | CH₃ | 3-(2-cyanophenoxy)-phenyl | 6.80–7.67(m, 9H); 3.60(s, 3H); 2.80(s, 6H); 2.48(d, 6H). |
| 7.17 | CH₃ | 3-isopropylphenyl | |
| 7.18 | CH₃ | phenyl | |
| 7.19 | CH₃ | 3-(3,5-dimethylphenoxy)-phenyl | |
| 7.20 | CH₃ | 3-(2-chloro-4-methylphenoxy)-phenyl | |
| 7.21 | CH₃ | 3-(4-chloro-2-methylphenoxy)-phenyl | |
| 7.22 | CH₃ | 3-(3-cyanophenoxy)-phenyl | |
| 7.23 | CH₃ | 3-(4-cyanophenoxy)-phenyl | |
| 7.24 | CH₃ | 3-(2-trifluoromethyl-phenoxy)-phenyl | |
| 7.25 | CH₃ | 3-(3-trifluoromethyl-phenoxy)-phenyl | |
| 7.26 | CH₃ | 3-(4-trifluoromethyl-phenoxy)-phenyl | |
| 7.27 | CH₃ | [phenyl-O-phenyl with C(CH₃)=N-OCH₃ substituent] | |
| 7.28 | H | [phenyl-O-phenyl with C(CH₃)=N-OCH₃ substituent] | |
| 7.29 | CH₃ | 3-(3-chlorophenoxy)-phenyl | |
| 7.30 | CH₃ | 3-(3-methoxyphenoxy)-phenyl | |
| 7.31 | CH₃ | 3-(2-methylphenoxy)-phenyl | 7.65(s, 1H); 6.60–7.61(m, 8H); 3.55, 3.41, 2.75 and 2.24(4s, 3H each), 2.48(d, 6H). |
| 7.32 | CH₃ | 3-(2,5-dimethylphenoxy)-phenyl | |
| 7.33 | CH₃ | 3-(2,3-dimethylphenoxy)-phenyl | |
| 7.34 | CH₃ | 3-(3-methylphenoxy)-phenyl | |
| 7.35 | CH₃ | 3-benzyloxy-phenyl | |
| 7.36 | CH₃ | 3-(2-methylbenzyloxy)-phenyl | |

TABLE 7-continued

Structure: pyrimidine with R₂, S-CH₃, COOCH₃, C=CH-N(CH₃)₂, O-R₃ substituents

| Comp. No. | R₂ | R₃ | physical data ¹H-NMR (CDCl₃) or/and m.p. |
|---|---|---|---|
| 7.37 | CH₃ | 3-(2-chlorobenzyloxy)-phenyl | |
| 7.38 | CH₃ | 3-(2,5-dimethylbenzyloxy)-phenyl | |
| 7.39 | CH₃ | 3-(3-chlorobenzyloxy)-phenyl | |
| 7.40 | CH₃ | 3-(3-methylbenzyloxy)-phenyl | |
| 7.41 | CH₃ | 3-(4-chlorobenzyloxy)-phenyl | |
| 7.42 | CH₃ | 3-(3-methoxybenzyloxy)-phenyl | |
| 7.43 | CH₃ | 3-(2-cyanobenzyloxy)-phenyl | |
| 7.44 | CH₃ | 3-(phenylethoxy)-phenyl | |
| 7.45 | CH₃ | 3-(phenoxy-methyl)-phenyl | |
| 7.46 | CH₃ | phenyl-CH₂-O-N=C(CH₃)-phenyl | |
| 7.47 | CH₃ | 3-(2,5-dimethylphenoxy-methyl)-phenyl | |
| 7.48 | CH₃ | phenyl-CH₂-O-phenyl-C(CH₃)=N-OCH₃ | |
| 7.49 | CH₃ | phenyl-CH₂-O-phenyl-C(CH₃)=N-O-allyl | |
| 7.50 | CH₃ | phenyl-C(CH₃)=N-O-(3-chlorobenzyl) | |
| 7.51 | CH₃ | phenyl-C(CH₃)=N-O-(2,5-dichlorobenzyl) | |
| 7.52 | CH₃ | phenyl-C(CH₃)=N-O-(2,5-dimethylbenzyl) | |
| 7.53 | CH₃ | phenyl-C(CH₃)=N-O-(2-chlorobenzyl) | |
| 7.54 | CH₃ | phenyl-C(CH₃)=N-O-benzyl | |
| 7.55 | CH₃ | phenyl-O-CH(CH₃)-phenyl-Cl | |

TABLE 7-continued

Structure: pyrimidine core with N, S—CH₃, COOCH₃, C=CH—N(CH₃)₂, O—R₃, and R₂ substituents.

| Comp. No. | R₂ | R₃ | physical data $^1$H-NMR (CDCl$_3$) or/and m.p. |
|---|---|---|---|

7.56 CH₃ — [1-(4-chlorophenoxy)ethyl]phenyl group (with CH₃ on benzylic carbon, O linked to 4-Cl-phenyl)

7.57 CH₃ 3-(2-naphthyl)-phenyl 7.58 CH₃ 3-(4-methylphenyl)-phenyl 7.59 CH₃ 3-(2-pyridyl)-phenyl 7.60 CH₃ — 3-[5-(3-trifluoromethylisoxazolyl)]phenyl 7.61 H — 3-[5-(3-trifluoromethylisoxazolyl)]phenyl 7.62 CH₃ — 3-[1-(ethoxyimino)ethyl]phenyl 7.63 H — 3-[1-(ethoxyimino)ethyl]phenyl 7.64 CH₃ — 3-[5-(3-methylisoxazolyl)]phenyl TABLE 7-continued

[Structure: pyrimidine with S-CH₃, COOCH₃, C=CH-N(CH₃)₂, O-R₃, and R₂ substituents]

| Comp. No. | R₂ | R₃ | physical data ¹H-NMR (CDCl₃) or/and m.p. |
|---|---|---|---|
| 7.65 | H | [3-methyl-isoxazol-5-yl-m-tolyl group] | |
| 7.66 | CH₃ | [3-ethyl-isoxazol-5-yl-m-tolyl group] | |
| 7.67 | H | [3-ethyl-isoxazol-5-yl-m-tolyl group] | |
| 7.68 | CH₃ | [benzothiazole-O-aryl group] | |
| 7.69 | CH₃ | [benzothiazole-S-aryl group] | |
| 7.70 | CH₃ | 3-methoxyphenyl | 7.68(s, 1H); 7.20–7.30(m, 1H); 6.60–6.72(m, 3H); 3.78 and 3.60(2s, 3H each); 2.72(s, 6H); 2.50(d, 6H). |
| 7.71 | CH₃ | [3-n-propyl-isoxazol-5-yl-p-phenyl group] | |
| 7.72 | CH₃ | [4-(2-cyanoethoxy)phenyl] | |
| 7.73 | CH₃ | 3-(4-chlorophenyl)phenyl | |
| 7.74 | CH₃ | 3-(4-cyanophenyl)phenyl | |
| 7.75 | CH₃ | 3-(3-cyanophenyl)phenyl | |
| 7.76 | CH₃ | [4-(N-OC₃H₇n)(CH₃)C=N-phenyl group] | |

TABLE 7-continued $$R_2 \text{—} \underset{N}{\overset{N}{\diagup}} \overset{S\text{—}CH_3}{\underset{\underset{O\text{—}R_3}{|}}{\diagdown}} \overset{COOCH_3}{\underset{|}{C=CH\text{—}N(CH_3)_2}}$$

| Comp. No. | R₂ | R₃ | physical data ¹H-NMR (CDCl₃) or/and m.p. |
|---|---|---|---|
| 7.77 | CH₃ | (3-(1-methyl-pyrazol-5-yl)phenyl group) | |
| 7.78 | CH₃ | (3-(1,5-dimethyl-pyrazol-4-yl)phenyl group) | |
| 7.79 | CH₃ | 3-(2-cyanophenyl)phenyl | |
| 7.80 | CH₃ | 3-(2-methylphenyl)phenyl | |
| 7.81 | CH₃ | 3,5-dimethylphenyl | |

Example A: Activity against Powdery Mildrew *Sphaerotheca fuliginea*:

Plants of *Cucumis sativus* (cucumber), 7 days old (cotyledon stage), are sprayed to near run off with a suspension containing 100 mg/l of active ingredient. The deposit is then allowed to dry. One day later, the treated plants are inoculated with a spore suspension containing 1×10⁵/ml of freshly collected conidia of *Sphaerotheca fuliginea* and then incubated in the greenhouse for 7 days at +24° C. and 60% r.h. The efficacy of the test compounds is determined by comparing the degree of fungal attack with that on untreated, similarly inoculated check plants. In this test compounds 1.01, 1.04, 1.08, 1.10, 1.13, 1.16, 1.17, 1.18, 1.24, 1.35, 1.39, 1.43, 1.50, 1.60, 1.62, 1.66, 1.73, 1.76, 1.79, 1.81, 2.18, 2.30, 2.41 and 2.54 showed an efficacy of more than 90%.

Similar methods are used to test the compounds against the following pathogens: *Podosphaera leucotricha* on apple,

*Erysiphe graminis* on wheat and barley (dry inoculation) where compounds 1.04, 1.08, 1.10, 1.11, 1.12, 1.13, 1.17, 1.18, 1.35, 1.36, 1.39, 1.44, 1.50, 1.60, 1.62, 1.76, 1.81, 2.30, 2.41 and 2.54 showed an efficacy of more than 90%, and

*Uncinula necator* on grape where compounds 1.16, 1.31, 1.70 and 2.18 showed an efficacy of more than 90%..

Example B: Activity against Rust, Scab, Pyrenophora, Leptosphaeria Uyces appendiculatus:

Plants of *Phaseolus vulgaris* (pole bean), 14 days old (2 leaves stage), are sprayed to near run off with a suspension containing 100 mg/l of the active ingredient. The deposit is then allowed to dry. One day later, the treated plants are inoculated with a spore suspension containing 1×10⁵/ml of freshly collected spores of Uromyces_appendiculatus. Incubation is performed for 3 days in a high humidity cabinet at +23° C. and >95% r.h. and thereafter during 10 days at +24° C. and 60% r.h.

The efficacy the compounds is determined by comparing the degree of fungal attack with that on untreated, similarly inoculated check plants. In this test compounds 1.04, 1.08, 1.10, 1.11, 1.12, 1.13, 1.16, 1.17, 1.35, 1.36, 1.39, 1.41, 1.42, 1.50, 1.60, 1.62, 1.73, 1.76, 1.81, 2.18, 2.30, 2.41 and 2.54 showed an efficacy of a t least 90%.

Similar methods are used to test the compounds against the following pathogens:

Puccinia triticina on wheat (plants 10 days old) where compounds 1.04, 1.08, 1.10, 1.11, 1.12, 1.17, 1.18, 1.35, 1.36, 1.39, 1.50, 1.60, 1.62, 1.76, 2.18, 2.30 and 2.41 showed an efficacy of at least 90%,

*Pyrenophora graminea* on barley where compounds 1.02, 1.10, 1.12, 1.17, 1.18, 1.60, 1.62, 1.81 and 2.18 showed an efficacy of at least 90%, Leptosphaeria nodoram on wheat where compounds 1.02, 1.04, 1.08, 1.17, 1.18, 1.39, 1.50, 1.60, 1.62, 1.81, 2.18, 2.30 and 2.41 showed an efficacy of at least 90%, and *Venturia inaequalis* on apple (plants 21 days old; the spore suspension contains 1% malt) where compounds 1.04, 1.08, 1.11, 1.16, 1.31 and 1.70 showed an efficacy of at least 90%.

Example C: Activity against Downy Mildew

Plants of *Lycopersicon esculentum* (tomato) with 6 leaves, are sprayed to near run off with a spray suspension containing 100 mg/l of the active ingredient. The deposit is then allowed to dry. 1 day later, the treated plants are inoculated with a spore suspension containing 1×10⁵/ml of freshly collected sporangia of *Phytophthora infestans* and then incubated for 7 days in a high humidity cabinet at +18° C. and >95% r.h. The efficacy of the test compounds is determined by comparing the degree of fungal attack with that on untreated, similarly inoculated check plants. In this test compounds 1.01, 1.04, 1.08, 1.10, 1.11, 1.12, 1.13, 1.16, 1.17, 1.18, 1.31, 1.35, 1.36, 1.39, 1.43, 1.44, 1.60, 1.62, 1.66, 1.70, 1.76, 2.18, 2.30 and 2.54 showed efficacy of at least 90%.

A similar method is used to test the compounds against *Plasmopara viticola* on grape vine where compounds 1.04, 1.08, 1.11, 1.16, 1.31, 1.70 and 2.18 showed efficacy of at least 90%.

Example D: Activity after Seed Treatment

The compounds of the invention may also be used for seed treatment. The advantageous fungicidal activity is established by in vitro tests with the following pathogens:

*Pyrenophora graminea,*

*Ustilago nuda,*

*Gerlachia nivalis,*

*Leptoshpaeria nodorum.*

Autoclaved wheat seeds are inoculated with spores or mycelium of the pathogens and coated with different concentrations of the test compounds resulting in dosages of 50 g a.i./100 kg seed. The treated seeds are then placed on agar plates and the pathogens allowed to grow for 3–8 days at +24° C. in the dark.

The efficacy of the test compounds is determined by comparing the degree of fungal growth emerging from treated and untreated inoculated seeds.

To evaluate the crop plant tolerance of the compounds, healthy seeds of wheat and barley are coated with the dosages mentioned above. The seeds are then allowed to germinate in petri dishes on moist filter paper in high humidity at +18° C. for 10 days. Plant damage is recorded, comparing the growth of treated and untreated seedlings.

In this test compounds 1.16 and 2.18 showed an efficacy of at least 90% against Pyrenophora graminea.

We claim:

1. Compounds of formula I

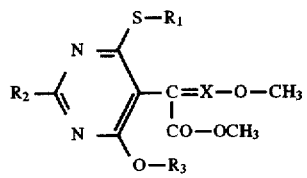

(I)

wherein $R_1$ is $C_{1-4}$alkyl, $R_2$ is hydrogen, $C_{1-4}$alkyl, or $C_{3-7}$cycloalkyl, $R_3$ is a radicle

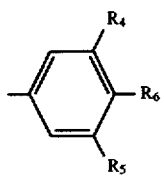

wherein $R_4$ is hydrogen, $C_{1-4}$alkyl, $C_{1-4}$haloalkyl, $C_{3-5}$alkenyloxy, $C_{3-5}$alkynyloxy, halogen, cyano, $C_{1-4}$alkoxy, $C_{1-4}$alkoxy-$C_{1-4}$alkoxy, cyano-$C_{1-4}$alkoxy, $C_{3-5}$alkenyl, $C_{3-7}$cycloalkyl, halo-$C_{3-7}$cycloalkyl, $C_{3-5}$alkynyl, $C_{1-4}$alkoxycarbonyl, —CONR$_9$R$_{10}$, —O—CONR$_9$R$_{10}$, —CR$_8$=N—O—R$_7$, phenyl, naphthyl, anthracenyl, phenoxy, naphthyloxy, anthracenyloxy, benzyloxy, 1-phenylethoxy 2-phenylethoxy, 3-phenylpropoxy, phenoxymethyl, phenyloxyethyl, phenoxypropyl, pyridyllpyrimidinyl, thienyl, ozazolyl, oxadiazolyl, triazolyl, thiadiazolyl, furyl, isoxazolyl, thiazolyl, imidazolyl, pyridazinyl, quinolinyl, guinazolinyl, benzimidazolyl, pyrazolyl, benzothiazolyl, benzoxazolyl, pyridyloxy, pyrimidinyloxy, thienyloxy, oxazolyloxy, oxadiazolyloxy, triazolyloxy, thiadiazolyloxy, furyloxy, isoxazolyloxy, thiazolyloxy, imidazolyloxy, pyridazinyloxy, auinolinyloxy, puinazolinyloxy, benzimidazolyloxy, frazolyloxy, benzothiazolyloxy, benzoxazolyloxy, phenoxymethoxy, 1-phenoxyethoxy, 2-phenoxvethoxy, 3-phenoxypropoxy or 2-phenoxylpropoxyl wherein each of the aromatic rings may be optionally substituted with no more than two substituents independently selected from the group of halogen, $C_{1-4}$alkyl, $C_{1-4}$alkoxy, $C_{1-4}$haloalkyl, cyano and nitro, $R_5$ is hydrogen, halogen, $C_{1-4}$alkoxy or $C_{1-4}$alkyl, $R_6$ is hydrogen, $C_{1-4}$alkyl, $C_{1-4}$alkoxy, cyano, nitro or halogen, $R_7$ is $C_{1-4}$alkyl, $C_{3-5}$alkenyl, $C_{1-4}$alkynyl, phenyl-$C_{1-4}$alkyl, or naphthyl-$C_{1-4}$alkyl.

$R_8$ is hydrogen, $C_{1-4}$alkyl, $C_{1-4}$alkoxy, di-$C_{1-4}$alkylamino, $C_{1-4}$halo alkyl, halogen, cyano, $C_{1-4}$alkoxycarbonyl, or $C_{1-7}$cycloalkyl, $R_9$ and $R_{10}$ are independently hydrogen or $C_{1-4}$alkyl, or together $C_{3-6}$alkylene or;

$C_{3-6}$alkylene interrupted by oxygen or sulfur, and

X is CH or nitrogen.

2. A compound according to claim 1, wherein $R_2$ and $R_8$ are independently each hydrogen or methyl.

3. A compound according to claim 1, wherein $R_1$ is methyl.

4. A compound according to claim 1, wherein $R_2$ is methyl.

5. A compound according to claim 1, wherein $R_5$ is hydrogen or methyl.

6. A compound according to claim 1, wherein $R_6$ is hydrogen.

7. A compound according to claim 1, wherein X is CH.

8. A compound according to claim 1 wherein $R_4$ is $C_{1-4}$alkyl, $C_{1-4}$haloalkyl, phenyl, phenoxy, cyanophenoxy, chlorophenoxy, methylphenoxy, dimethylphenoxy, trifluoromethylphenoxy, halogen, cyano, benzyloxy, isoxazolyl, benzothiazolyloxy, $C_{1-4}$alkoxy, or the group —C(CH$_3$)=N—O—R$_7$, wherein R$_7$ is $C_{1-4}$alkyl, allyl, propargyl or benzyl.

9. A compound according to claim 1, wherein $R_4$ is pyrazolyl.

10. A compound according to claim 1, wherein $R_1$ and $R_2$ are methyl, $R_5$ and $R_6$ are hydrogen, and $R_4$ is $C_{1-4}$alkyl, C4haloalkyl, phenyl, phenoxy, cyanophenoxy, chlorophenoxy, methylphenoxy, dimethylphenoxy, trifluoromethylphenoxy, halogen, cyano, benzyloxy, isoxazolyl, benzothiazolyloxy, $C_{1-4}$alkoxy, or the group —C(CH$_3$)=N—O—R$_7$, wherein R$_7$ is $C_{1-4}$alkyl, allyl, propargyl or benzyl.

11. A compound according to claim 1 wherein $R_1$ and $R_2$ are methyl, $R_5$ and $P_4$ are hydrogen, and $R_4$ is pyrazolyl.

12. A compound according to claim 10, wherein X is CH.

13. A compound according to claim 1 of formula Ia

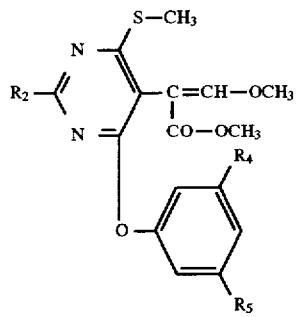

wherein

R$_2$ is hydrogen or methyl,

R$_4$ is hydrogen, phenyl, isoxazolyl, C$_{1-4}$alkyl, —CH$_2$—O-phenyl, —CH$_2$—O—CH$_2$-phenyl, —C(CH$_3$)=N—O—C$_{1-4}$alkyl, —C(CH$_3$)=N—O—C$_{3-4}$alkenyl, —C(CH$_3$)=—N—OCH$_2$-phenyl, wherein phenyl may be optionally substituted by one or two radicals independently selected from halogen, C$_{1-4}$alkyl, C$_{1-4}$alkoxy or cyano; or is phenoxy optionally substituted by one to three radicals selected from C$_{1-4}$alkyl, cyano, nitro, halogen, C$_{1-4}$haloalkyl, C$_{1-4}$-alkoxy, or C$_{1-4}$haloalkoxy; and R$_5$ is hydrogen or methyl.

14. A compound of formula Ia as defined in claim 13 wherein R$_2$ and R$_5$ are as defined in claim 13, and R$_4$ is pyrazolyl.

15. A compound according to claim 1, selected from the group comprising methyl α-[2-methyl-4-methylthio6-(3-trifluoromethyl-phenoxy)-pyrimidin-5-yl]-β-methoxyacrylate;

methyl α-[2-methyl-4-methylthio-6-(3-(2-yanophenoxy)-phenoxy)-pyrimidin-5-yl]-β-methoxyacrylate;

ethyl α-[2-methyl4-methylthio-6-(3-methoxy-phenoxy)-pyrimidin-5-yl]-β-methoxyacrylate;

methyl α-[2-methyl4-methylthio-6-(3-(3-chlorobenzyloxy)-phenoxy) -pyrimidin-5-yl]-β-methoxyacrylate;

methyl α-[2-methyl4-methylthio-6-(3-isopropyl-5-methyl-phenoxy)-pyrimidin-5-yl]-β-methoxyacrylate;

methyl α-[2-methyl4-methylthio-6-(3-(1-methyl-2-ethoxyimino)-phenoxy)-pyrimidin-5-yl]-β-methoxyacrylate;

methyl α-[4-methyl-6-(3-(1-methyl-2-ethoxyimino)-phenoxy)-pyrimidin-5-yl]-β-methoxyacrylate;

methyl α-[4-methylthio-6-(3-(1-methyl-2-ethoxyimino)-phenoxy)-pyrimidin-5-yl]β-methoxyacrylate;

methyl α-[2-methyl4-methylthio-6-(3-(4-chlorophenyl)-phenoxy)-pyrimidin-5-yl]-β-methoxyacrylate;

methyl α-[2-methyl4-methylthio-6-(3-(3-cyanophenyl)-phenoxy)-pyrimidin-5-yl]-β-methoxyacrylate;

methyl α-[2-methyl4-methylthio-6-(3-(2-methylphenyl)-phenoxy)-pyrimidin-5-yl]-β-methoxyacrylate;

methyl 2-methoximino-2-[2-methyl4-methylthio-6-(3-tert.-butyl-phenoxy)-pyrimidin-5-yl]-acetate; and methyl 2-methoxyimino-2-[2-methyl4-methylthio-6-(3-(2-cyanophenoxy)-phenoxy)-pyrimidin-5-yl]-acetate.

16. Method of combatting phytopathogenic fungi comprising applying to the fungi or their habitat a fungicidally effective amount of a compound of formula I according to claim 1.

17. Fungicidal composition comprising a compound of formula I stated in claim 1 and a agriculturally acceptable diluent.

* * * * *